US008633180B2

(12) United States Patent
Li et al.

(10) Patent No.: US 8,633,180 B2
(45) Date of Patent: Jan. 21, 2014

(54) ORGANIC COMPOUNDS

(75) Inventors: Peng Li, New York, NY (US); Jun Zhao, New York, NY (US); Hailin Zeng, New York, NY (US); Lawrence Wennogle, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 198 days.

(21) Appl. No.: 13/133,082

(22) PCT Filed: Dec. 7, 2009

(86) PCT No.: PCT/US2009/006442
§ 371 (c)(1),
(2), (4) Date: Jun. 6, 2011

(87) PCT Pub. No.: WO2010/065151
PCT Pub. Date: Jun. 10, 2010

(65) Prior Publication Data
US 2012/0071450 A1 Mar. 22, 2012

Related U.S. Application Data

(60) Provisional application No. 61/120,441, filed on Dec. 6, 2008.

(51) Int. Cl.
*A61K 31/565* (2006.01)
*A61K 31/57* (2006.01)
*A61K 31/519* (2006.01)
*C07D 487/14* (2006.01)

(52) U.S. Cl.
USPC .................... 514/171; 514/257; 544/247

(58) Field of Classification Search
USPC .................... 514/171, 257; 544/247
See application file for complete search history.

(56) References Cited

U.S. PATENT DOCUMENTS

| | | | |
|---|---|---|---|
| 5,202,328 A | 4/1993 | De Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,939,419 A | 8/1999 | Tulshian |
| 6,013,621 A | 1/2000 | Nishi et al. |
| 6,133,273 A | 10/2000 | Gilbert et al. |
| 6,235,742 B1 | 5/2001 | Bell et al. |
| 6,492,371 B2 | 12/2002 | Roylance |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2005/0075795 A1 | 4/2005 | Pandit |
| 2005/0113379 A1 | 5/2005 | Ge et al. |
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0094966 A1 | 4/2012 | Li et al. |
| 2012/0136013 A1 | 5/2012 | Li et al. |

FOREIGN PATENT DOCUMENTS

| | | |
|---|---|---|
| DE | 19931206 | 1/2001 |
| EP | 0201188 | 12/1986 |
| EP | 0636626 | 2/1995 |
| EP | 0911333 | 4/2002 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 01/27113 | 4/2002 |
| WO | WO 02/74312 | 9/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |
| WO | WO 2007/143568 | 12/2007 |

(Continued)

OTHER PUBLICATIONS

"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chern. (1997) 40(14):2196-2210.
Banker, Gilbert S. et al., Modem Pharmaceutics, Marcel Dekker, New York, 1996.
Bender et al., "Cyclic Nucleotide Phosphodiesterases: Molecular Regulation to Clinical Use" PharmcoL Rev., 2006, 58, pp. 488-520.
Chebib et al., 1-Phenylpyrazolo[3,4-d]pyrimidines; Structure-Activity Relationships for C6 Substituents at $A_1$ and $A_{2A}$ Adenosine Receptors Bioorganic & Medicinal Chemistry (2000) 8:2581-2590.

(Continued)

*Primary Examiner* — Kristin Vajda
(74) *Attorney, Agent, or Firm* — Hoxie & Associates, LLC

(57) ABSTRACT

Optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(optionally 4-thioxo or 4-imino)-(1H or 2H)-pyrimido[1,2-a]pyrazolo[4,3-e]pyrimidine compounds or Compounds of Formula (I), processes for their production, their use as pharmaceuticals and pharmaceutical compositions comprising them.

32 Claims, No Drawings

(56) References Cited

FOREIGN PATENT DOCUMENTS

| WO | WO 2007/143705 | 12/2007 |
|----|----------------|---------|
| WO | WO 2008/063505 | 5/2008 |
| WO | WO 2009/073210 | 6/2009 |
| WO | WO 2009/075784 | 6/2009 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |

OTHER PUBLICATIONS

Dewald et al., Synthesis and Potential Antipsychotic Activity of 1 H-Imidazo[1.2-c]pyrazolo[3,4-e]pyrimidines, J. Med. Chem. 1988, 31, pp. 454-461.

Fienberg et al., "DARPP-32: Regulator of the Efficacy of Dopaminergic Neurotransmission", Science, (1998) 281, pp. 838-842.

Greengard et al., "Beyond the Dopamine Receptor: the DARPP-32 Protein Phosphatase-1 Cascade", Neuron, 1999,23, pp. 435,447.

Han et al., "The Calcium/Calmodulin-dependent Phosphodiesterase PDE1C Downregulates Glucose-induced Insulin Secretion", J. Bio, Chem., 1999,274(32), pp. 22337-22344.

Jiang, et al., Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol, J. Org. Chem., 70, 2824-2827 (2004).

Mani et al., Science (2000) 287: 1053.

Murray et al., "Expression and activity of cAMP phosphodiesterase isoforms in pulmonary artery smooth muscle cells from patients with pulmonary hypertension: role for PDE1", Am. J. Physiol. Lunr:I Cell Mol. Physiol. 2007, 292, pp. L294-L303.

Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).

Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.

Porsolt et al. Nature (1977) 266:730-732.

Poulsen et al.HIgh-Pressure Synthesis of Enantiomerlcally Pure C-6 Substituted Pyrazolo[3,4-d]pyrimidines Biorganic & Medicinal Chemistry letter (2001) 11:191-193.

Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.

Rybalkin et al., "Cyclic GMP Phosphodiesterases and Regulation of Smooth Muscle Function", Circ. Res. 2003,93, pp. 280-291.

Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", Cancer Research, 2004, 64, pp. 2568-2571.

Turko et al., Inhibition of Cyclic GMP-Binding Cyclic GMP-Specific Phosphodiesterase (Type 5) by Sildenafil and Related Compounds Molecular Pharmacology (1990) 56:124-130.

Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).

Wolff, Manfred E., Burger's Medicinal Chemistry and Drug Discovery, Fifth Ed., vol. 1: Principles and Practice, John Wiley & Sons, 1995, 975.

Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).

Al-Afaleq, E., et al., "Heterocyclic o-Aminonitriles: Preparation of Pyrazolo[3,4-d]-pyrimidines with Modification of the substituents at the 1-position", *Molecules*, 6, pp. 621-638, (2001).

Blokland, "PDE Inhibition and Cognition Enhancement", vol. 22 No. 4, pp. 349-354 (2012) (Abstract Only).

Gelbin, et al., "Ketene-S, N-acetals as synthons for heterocycles new synthesis of pyrimidinones", *Journal Fuer Praktische Chemie*, vol. 329, No. 5, pp. 753-766, (1987).

Goodman & Gilman, The Pharmacological Basis of Therapeutics, McGraw-Hill Interamericana. 2007, p. 892.

Office Action from related U.S. Appl. No. 13/133,101 mailed on Feb. 5, 2013.

Office Action from related U.S. Appl. No. 13/133,033 mailed on Feb. 6, 2013.

\* cited by examiner

US 8,633,180 B2

ORGANIC COMPOUNDS

CROSS REFERENCE TO RELATED APPLICATIONS

This application is a United States Application under 35 U.S.C. 371 claiming benefit of PCT Application No. PCT/US2009/006442, filed on Dec. 7, 2009, which claims the benefit of U.S. provisional application 61/120,441, filed on Dec. 6, 2008, the contents of each of which are incorporated herein by reference.

TECHNICAL FIELD

The present invention relates to optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(optionally 4-thioxo or 4-imino)-(1H or 2H)-pyrimido[1,2-a]pyrazolo[4,3-e]pyrimidine compounds, preferably Compounds of Formula I as described below, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1A and/or PDE1B activity.

SUMMARY OF THE INVENTION

The invention provides optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4

(5H)-thione or 7,8-dihydro-2H-imidazo[1,2-a]pyrazolo[4,3-e]pyrimidine-4(5H)-thione compounds, e.g., a Compound of Formula II:

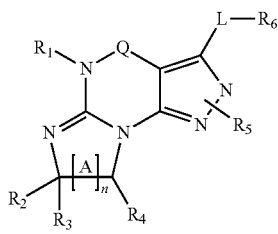

Formula II wherein
(i) Q is C(=S), C(=N($R_{20}$)) or $CH_2$;
(ii) L is a single bond, —N(H)—, —$CH_2$—;
(iii) $R_1$ is H or $C_{1-4}$ alkyl (e.g., methyl or ethyl);
(iv) $R_4$ is H or $C_{1-6}$ alkyl (e.g., methyl, isopropyl) and $R_2$ and $R_3$ are, independently:
H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)arylalkoxy,
(optionally hetero)aryl$C_{1-6}$alkyl, or
$R_2$ and $R_3$ together form a 3- to 6-membered ring;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is
a) -D-E-F, wherein:
D is $C_{1-4}$alkylene (e.g., methylene, ethylene or prop-2-yn-1-ylene);
E is a single bond, $C_{2-4}$alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
halo$C_{1-4}$alkyl (e.g., trifluoromethyl),
—C(O)—$R_{15}$,
—N($R_{16}$)($R_{17}$),
—S(O)$_2R_{21}$ or
$C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
$C_{1-4}$alkyl (e.g., methyl),
halo$C_{1-4}$alkyl (e.g., trifluoromethyl),
$C_{1-4}$alkoxy) or
$C_{1-4}$alkyl (e.g., 5-methylpyrid-2-yl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl),
or F is aryl, e.g., phenyl, substituted with one or more halo (e.g., 4-fluorophenyl)
or F is a $C_{3-7}$heterocycloalkyl (e.g., pyrrolidinyl) optionally substituted with a $C_{1-6}$alkyl (e.g., 1-methylpyrrolidin-3-yl); or
b) a substituted heteroarylalkyl, e.g., substituted with haloalkyl;
c) attached to one of the nitrogens on the pyrazolo portion of Formula I and is a moiety of Formula A

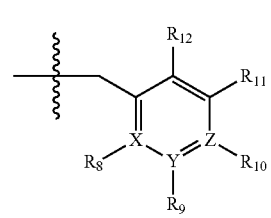

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl,
$C_{3-7}$cycloalkyl,
het$C_{3-7}$cycloalkyl (e.g., pyrrolidinyl or piperidinyl),
$C_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently and optionally substituted with one or more halo (e.g., F or Cl), $C_{1-4}$alkyl, $C_{1-4}$alkoxy, $C_{1-4}$haloalkyl (e.g., trifluoromethyl), —SH;
preferably $R_{10}$ is phenyl, pyridyl, piperidinyl or pyrrolidinyl optionally substituted with the substituents previously defined, e.g. optionally substituted with halo or alkyl
provided that when X, Y, or Z is nitrogen, $R_8$, $R_9$, or $R_{10}$, respectively, is not present;
(vi) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or —N($R_{18}$)($R_{19}$);
wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl, (vii) n=0 or 1;

(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a bridge with $R_2$ or $R_4$;

(ix) $R_{15}$ is $C_{1-4}$alkyl, halo$C_{1-4}$alkyl, —OH or —O$C_{1-4}$alkyl (e.g., —OCH$_3$)

(x) $R_{16}$ and $R_{17}$ are independently H or $C_{1-4}$alkyl;

(xi) $R_{18}$ and $R_{19}$ are independently
H,
$C_{1-4}$alky,
$C_{3-8}$cycloalkyl,
hetero$C_{3-8}$cycloalkyl,
aryl (e.g., phenyl), or
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, or
$C_{3-8}$cycloalkyl;

(xii) $R_{20}$ is H, $C_{1-4}$alkyl (e.g., methyl) or $C_{3-7}$cycloalkyl, (xiii) $R_{21}$ is $C_{1-6}$alkyl;

in free or salt form.

In another embodiment, the invention provides a Compound of Formula I:

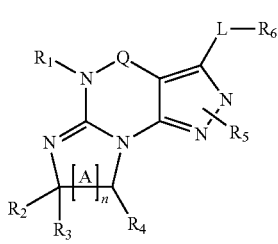

Formula I wherein
(i) Q is C(=S), C(=N($R_{20}$)) or CH$_2$;
(ii) L is a single bond, —N(H)—, —CH$_2$—;
(iii) $R_1$ is H or $C_{1-4}$ alkyl (e.g., methyl or ethyl);
(iv) $R_4$ is H or $C_{1-6}$ alkyl (e.g., methyl, isopropyl) and $R_2$ and $R_3$ are, independently, H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$alkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(v) $R_5$ is
a) -D-E-F, wherein:
D is $C_{1-4}$alkylene (e.g., methylene, ethylene or prop-2-yn-1-ylene);
E is a single bond, $C_{2-4}$alkynylene (e.g., —C≡C—), arylene (e.g., phenylene) or heteroarylene (e.g., pyridylene);
F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl), —C(O)—$R_{15}$, —N($R_{16}$)($R_{17}$), —S(O)$_2$$R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
$C_{1-4}$alkyl (e.g., methyl),
halo$C_{1-4}$alkyl (e.g., trifluoromethyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl),
or F is aryl, e.g., phenyl, substituted with one or more halo (e.g., 4-fluorophenyl)
or F is a $C_{3-7}$heterocycloalkyl (e.g., pyrrolidinyl) optionally substituted with a $C_{1-4}$alkyl (e.g., 1-methylpyrrolidin-3-yl);
or
b) a substituted heteroarylalkyl, e.g., substituted with haloalkyl;
c) attached to one of the nitrogens on the pyrazolo portion of Formula I and is a moiety of Formula A

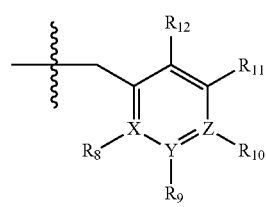

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl,
$C_{3-7}$cycloalkyl,
$C_{1-4}$haloalkyl (e.g., trifluoromethyl),
aryl (e.g., phenyl),
heteroaryl (e.g., pyridyl (for example pyrid-2-yl), or
thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, $R_8$, $R_9$, or $R_{10}$, respectively, is not present;

(vi) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$alkoxy, for example, $R_6$ is 4-hydroxyphenyl or 4-fluorophenyl,
(vii) n=0 or 1;
(viii) when n=1, A is —C($R_{13}R_{14}$)—, wherein $R_{13}$ and $R_{14}$ are, independently, H or $C_{1-4}$alkyl, aryl, heteroaryl, (optionally hetero)aryl$C_{1-4}$alkoxy or (optionally hetero)aryl$C_{1-4}$alkyl;
(ix) $R_{15}$ is $C_{1-4}$alkyl, halo$C_{1-4}$alkyl, —OH or —O$C_{1-4}$alkyl (e.g., —OCH$_3$)
(x) $R_{16}$ and $R_{17}$ are independently H or $C_{1-4}$alkyl;
(xi) $R_{18}$ and $R_{19}$ are independently H, $C_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xii) $R_{20}$ is H, $C_{1-4}$alkyl (e.g., methyl) or $C_{3-7}$cycloalkyl,
(xiii) $R_{21}$ is $C_{1-6}$alkyl;
in free or salt form.

The invention further provides compounds of Formula I as follows:

1.1 Formula I, wherein Q is C(=S), C(=N($R_{20}$)) or CH$_2$;
1.2 Formula I or 1.1, wherein Q is C(=S);
1.3 Formula I or 1.1, wherein Q is C(=N($R_{20}$));
1.4 Formula I or 1.1, wherein Q is CH$_2$;
1.5 Formula I, or any of 1.1-1.4, wherein L is a single bond, —N(H)—, or —CH$_2$—;
1.6 Formula 1.5, wherein L is a single bond;
1.7 Formula 1.5, wherein L is —N(H)—;
1.8 Formula 1.5, wherein L is —CH$_2$—;
1.9 Formula I, or any of 1.1-1.8, wherein $R_1$ is H or $C_{1-4}$ alkyl (e.g., methyl);
1.10 Formula 1.9, wherein $R_1$ is H,
1.11 Formula 1.9, wherein $R_1$ is $C_{1-4}$ alkyl (e.g., methyl or ethyl);
1.12 Formula I, or any of 1.1-1.11, wherein $R_4$ is H or $C_{1-6}$ alkyl (e.g., methyl, isopropyl) and $R_2$ and $R_3$ are, independently, H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$alkyl;
1.13 Formula 1.12, wherein $R_2$ or $R_3$ is H or $C_{1-6}$alkyl (e.g., methyl or isopropyl);
1.14 Formula 1.12, wherein $R_2$ or $R_3$ is H,
1.15 Formula 1.12, wherein $R_2$ or $R_3$ is $C_{1-6}$alkyl (e.g., methyl or isopropyl);
1.16 Formula 1.12, wherein $R_2$ or $R_3$ is methyl;
1.17 Formula 1.12, wherein $R_2$ or $R_3$ is isopropyl;
1.18 Formula I, or any of 1.1-1.11, wherein $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
1.19 Formula I or any of 1.1-1.18, wherein $R_5$ is -D-E-F;
1.20 Formula 1.19, wherein D is $C_{1-4}$alkylene (e.g., methylene, ethylene or prop-2-yn-1-ylene);
1.21 Formula 1.20, wherein D is methylene;
1.22 Any of formulae 1.19-1.21, wherein E is a single bond, $C_{2-4}$alkynylene (e.g., arylene (e.g., phenylene) or heteroarylene (e.g., pyridylene);
1.23 Any of formulae 1.19-1.21, wherein E is arylene (e.g., phenylene);
1.24 Any of formulae 1.19-1.21, wherein E is phenylene;
1.25 Any of formulae 1.19-1.21, wherein E is heteroarylene (e.g., pyridylene);
1.26 Any of formulae 1.19-1.21, wherein E is phenylene wherein F is para-substituted;
1.27 Any of formulae 1.19-1.21, wherein E is heteroarylene (e.g., pyridylene);
1.28 Any of formulae 1.19-1.21, wherein E is a single bond;
1.29 Any of formulae 1.19-1.28, wherein F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl), —C(O)—$R_{15}$, —N($R_{16}$)($R_{17}$), —S(O)$_2R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
1.30 Formula 1.29, wherein F is halo$C_{1-4}$alkyl (e.g., trifluoromethyl);
1.31 Formula 1.29, wherein F is trifluoromethyl;
1.32 Formula 1.29, wherein F is halo (e.g., F, Br, Cl);
1.33 Formula 1.29, wherein F is Cl;
1.34 Formula 1.29, wherein F is heteroaryl (e.g., pyridyl, e.g., pyrid-2-yl);
1.35 Formula 1.29, wherein F is pyridyl;
1.36 Formula 1.29, wherein F is pyrid-2-yl;
1.37 Formula 1.29, wherein F is $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, morpholinyl);
1.38 Formula 1.29, wherein F is cyclohexyl;
1.39 Formula 1.29, wherein F is pyrrolidinyl (e.g., pyrrolidin-3-yl);
1.40 Formula 1.29, wherein F is cyclopentyl;
1.41 Formula 1.29, wherein F is tetrahydro-2H-pyran-4-yl;
1.42 Formula 1.29, wherein F is aryl (e.g., phenyl);
1.43 Formula 1.29, wherein F is phenyl;
1.44 Formula 1.29, wherein F is 4-chlorophenyl;
1.45 Formula 1.29, wherein F is —S(O)$_2R_{21}$ wherein $R_{21}$ is $C_{1-6}$alkyl (e.g., methyl);
1.46 Formula 1.29, wherein F is —C(O)—$R_{15}$ and $R_{15}$ is $C_{1-4}$alky (e.g., methyl), halo$C_{1-4}$alkyl (e.g., trifluoromethyl), —OH or —O$C_{1-4}$alkyl (e.g., —OCH$_3$);
1.47 Any of formulae 1.19-1.46, wherein D, E and F are independently and optionally substituted with one or more halo (e.g., F, Cl or Br), $C_{1-4}$alkyl (e.g., methyl), halo$C_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl), or F is aryl, e.g., phenyl, substituted with one or more halo (e.g., 4-fluorophenyl), or F is a or F is a $C_{3-7}$heterocycloalkyl (e.g., pyrrolidinyl) optionally substituted with a $C_{1-6}$alkyl (e.g., 1-methylpyrrolidin-3-yl);

1.48 Formula 1.47, wherein F is substituted with one or more halo (e.g., F, Cl or Br), $C_{1-4}$alkyl (e.g., methyl), halo$C_{1-4}$alkyl (e.g., trifluoromethyl);

1.49 Formula 1.47, wherein F is 6-fluoropyrid-2-yl;

1.50 Formula 1.47, wherein F is 3-fluoropyrid-2-yl;

1.51 Formula 1.47, wherein F is 4-fluoropyrid-2-yl;

1.52 Formula 1.47, wherein F is 5-fluoropyrid-2-yl;

1.53 Formula 1.47, wherein F is heteroaryl, e.g., pyridyl, optionally substituted with one or more halo$C_{1-4}$alkyl (e.g., 5-trifluoromethylpyrid-2-yl;

1.54 Formula 1.47, wherein F is 5-trifluoromethylpyrid-2-yl;

1.55 Formula 1.47, wherein F is heteroaryl, e.g., pyridyl, optionally substituted with one or more $C_{1-4}$alkyl (e.g., 5-methylpyrid-2-yl);

1.56 Formula 1.47, wherein F is 5-methylpyrid-2-yl;

1.57 Formula 1.29, wherein F is —C(O)—$R_{15}$ and $R_{15}$ is methyl;

1.58 Formula 1.29, wherein F is —C(O)—$R_{15}$ and $R_{15}$ is trifluoromethyl;

1.59 Formula 1.29, wherein F is —C(O)—$R_{15}$ and $R_{15}$ is —OH;

1.60 Formula 1.29, wherein F is —C(O)—$R_{15}$ and $R_{15}$ is —O$C_{1-4}$alkyl (e.g., —OCH$_3$);

1.61 Formula 1.29, wherein F is —C(O)—$R_{15}$ and $R_{15}$ is —OCH$_3$;

1.62 Formula 1.29, wherein F is —N($R_{16}$)($R_{17}$);

1.63 Formula I or any of 1.1-1.18, wherein $R_5$ is a substituted heteroarylalkyl, e.g., substituted with haloalkyl;

1.64 Formula I or any of 1.1-1.18, wherein $R_5$ is attached to one of the nitrogens on the pyrazolo portion of Formula I and is a moiety of Formula A

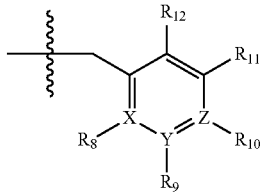

Formula A wherein X, Y and Z are, independently, N or C, and $R_8$, $R_9$, $R_{11}$ and $R_{12}$ are independently H or halogen (e.g., Cl or F), and $R_{10}$ is halogen, $C_{1-4}$alkyl, $C_{3-7}$cycloalkyl, $C_{1-4}$haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present 1.65 Formula 1.64, wherein $R_5$ is a substituted heteroarylmethyl, e.g., para-substituted with haloalkyl;

1.66 Formula 1.64, wherein $R_5$ is a moiety of Formula A wherein $R_8$, $R_9$, $R_{11}$, and $R_{12}$ are H and $R_{10}$ is phenyl;

1.67 Formula 1.64, wherein $R_5$ is a moiety of Formula A wherein $R_8$, $R_9$, $R_{11}$, and $R_{12}$ are H and $R_{10}$ is pyridyl or thiadiazolyl;

1.68 Formula 1.64, wherein $R_5$ is a moiety of Formula A wherein $R_8$, $R_9$, $R_{11}$, and $R_{12}$ are, independently, H or halogen, and $R_{10}$ is haloalkyl;

1.69 Formula 1.64, wherein $R_5$ is a moiety of Formula A wherein $R_8$, $R_9$, $R_{11}$, and $R_{12}$ are, independently, H, and $R_{10}$ is alkyl sulfonyl;

1.70 Formula I or any of 1.1-1.69, wherein $R_6$ is H, $C_{3-7}$cycloalkyl (e.g., cyclopentyl), aryl, heteroaryl, aryl$C_{1-4}$alkyl (e.g., benzyl), arylamino (e.g., phenylamino), heterarylamino, N,N-di$C_{1-4}$alkylamino, N,N-diarylamino, N-aryl-N-(aryl$C_{1-4}$alkyl)amino (e.g., N-phenyl-N-(1,1'-biphen-4-ylmethyl)amino), or —N($R_{18}$)($R_{19}$), wherein the aryl or heteroaryl is optionally substituted with one or more halo (e.g., F, Cl), hydroxy or $C_{1-6}$alkoxy;

1.71 Formula 1.70, wherein $R_6$ is H, 1.72 Formula 1.70, wherein $R_6$ is $C_{1-4}$alkyl;

1.73 Formula 1.70, wherein $R_6$ is $C_{3-7}$cycloalkyl (e.g., cyclopentyl);

1.74 Formula 1.70, wherein $R_6$ is aryl (e.g., phenyl) optionally substituted with one or more halo (e.g., F, Cl), hydroxy or $C_{1-6}$alkoxy;

1.75 Formula 1.70, wherein $R_6$ is fluorophenyl (e.g., 4-fluorophenyl) or hydroxyphenyl (e.g., 4-hydroxyphenyl);

1.76 Formula I or any of 1.1-1.75, wherein n=0;

1.77 Formula I or any of 1.1-1.75, wherein n=1;

1.78 Formula 1.77, wherein n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy or (optionally hetero)aryl$C_{1-4}$alkyl;

1.79 any of the preceding formulae wherein the compound is selected from a group consisting of:

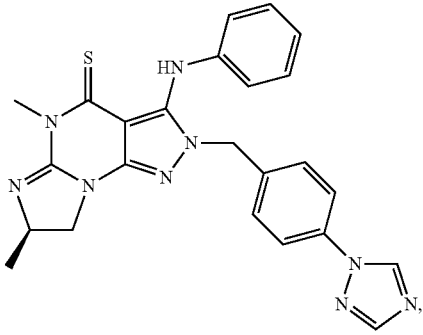

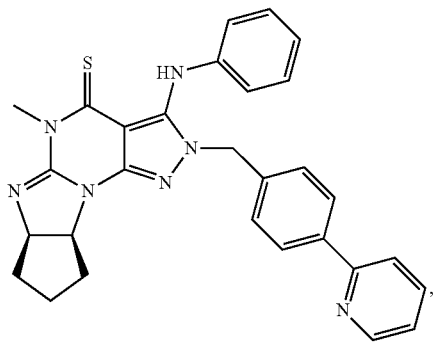

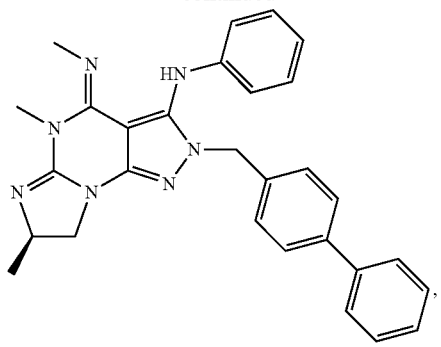
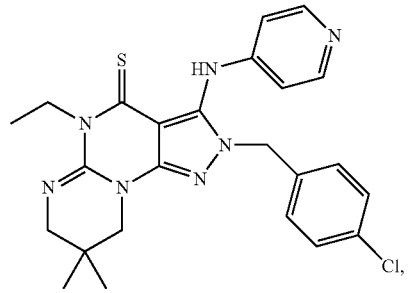
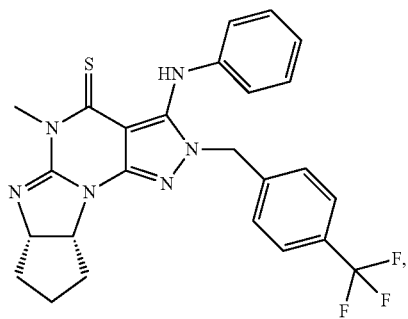
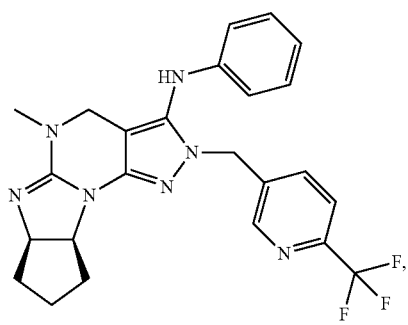
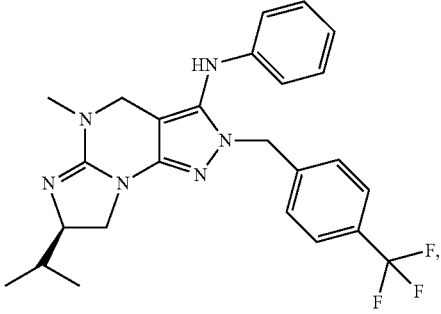
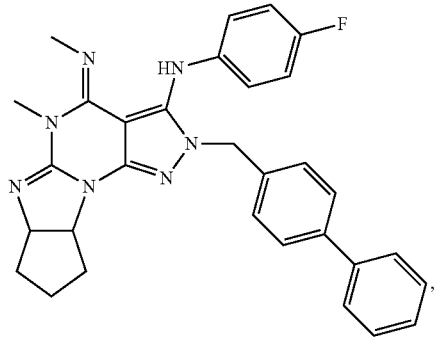
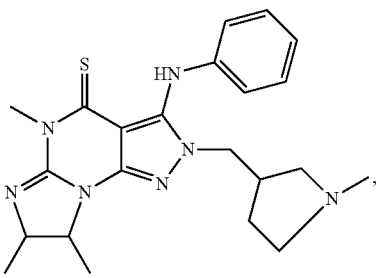
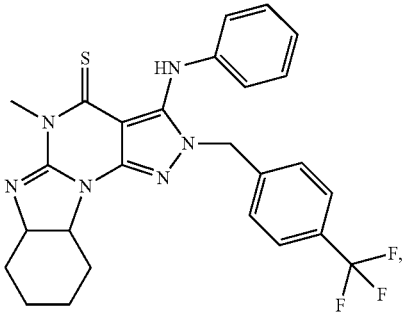
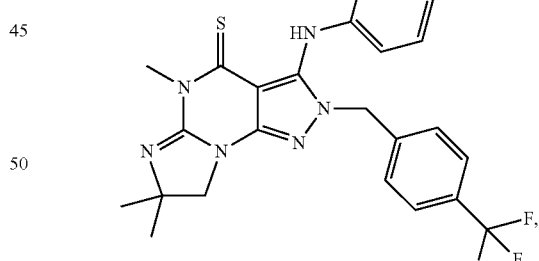
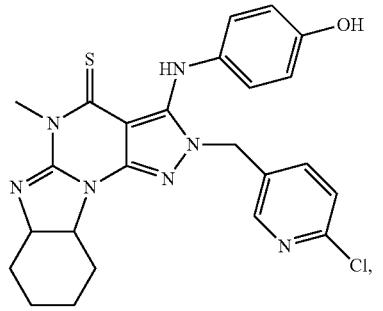

-continued

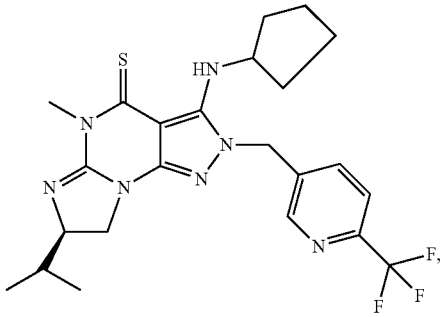

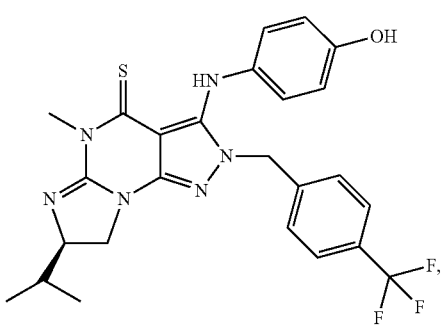

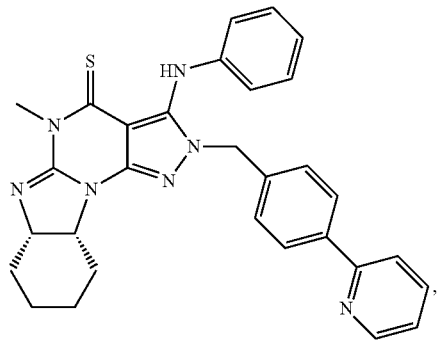

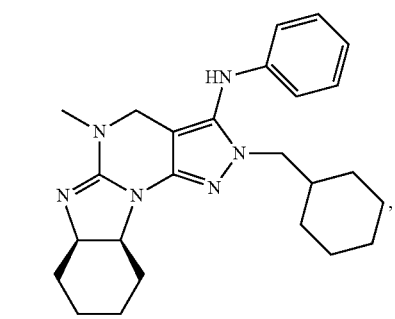

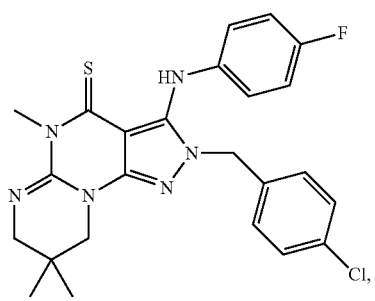

-continued

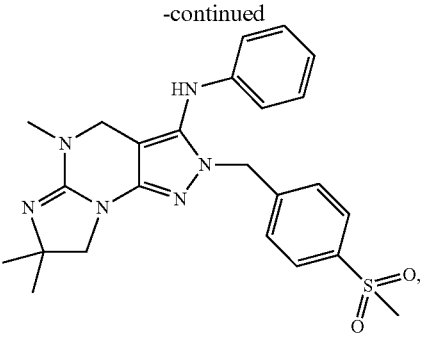

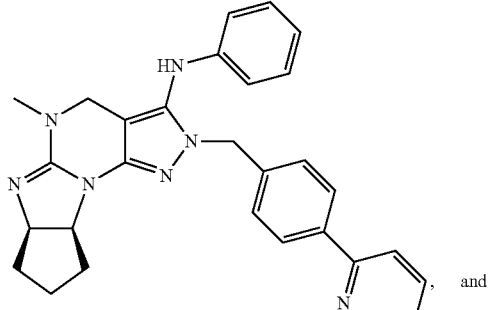

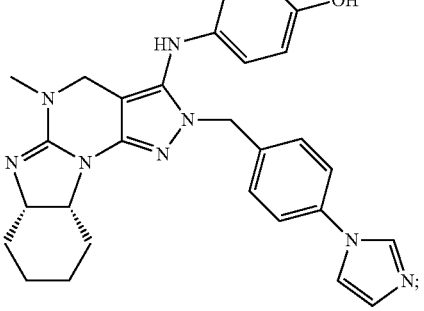

1.80 any of the preceding formulae wherein the compounds inhibit phosphodiesterase-mediated (e.g., PDE 1-mediated, especially PDE1B-mediated) hydrolysis of cGMP, e.g., with an $IC_{50}$ of less than 1 µM, preferably less than 500 nM, more preferably less than 50 nM in an immobilized-metal affinity particle reagent PDE assay, for example, as described in Example 12,
in free or salt form.

In one embodiment, the invention provides a compound of formula I or II as defined above, wherein:
(i) $R_6$ is
H,
$C_{1-4}$alkyl,
$C_{3-7}$cycloalkyl (e.g., cyclopentyl or cyclohexyl),
aryl (e.g., phenyl),
heteroaryl (e.g., pyridyl, for example, pyrid-4-yl),
aryl$C_{1-4}$alkyl (e.g., benzyl),
when L is a single bond, —N(H)—, —CH$_2$
wherein said aryl or heteroaryl is independently and optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl
or $R_6$ is
arylamino (e.g., phenylamino),
heterarylamino,
N,N-di$C_{1-4}$alkylamino, N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$),
when L is single bond or —CH$_2$—,
wherein the aryl or heteroaryl is optionally substituted with one or more halo (e.g., F, Cl), hydroxy, C$_{1-6}$alkyl, C$_{1-6}$alkoxy, C$_{3-8}$cycloalkyl, for example, R$_6$ is 4-hydroxyphenyl or 4-fluorophenyl,
and the rest of the substituents are as previously defined in Formula I or II or any of formulae 1.1-1.80, in free or salt form.

In still another embodiment, the invention provides a Compound of Formula II, wherein:
(i) R$_5$ is attached to one of the nitrogens on the pyrazolo portion of Formula II and is a moiety of Formula A

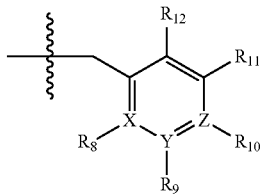

Formula A wherein X, Y and Z are, independently, N or C, and R$_8$, R$_9$, R$_{11}$ and R$_{12}$ are independently H or halogen (e.g., Cl or F), and R$_{10}$ is:
halogen,
C$_{1-4}$alkyl,
C$_{3-7}$cycloalkyl,
heteroC$_{3-7}$cycloalkyl (e.g., pyrrolidinyl or piperidinyl),
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl,
tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently and optionally substituted with one or more halo (e.g., F or Cl), C$_{1-4}$alkyl, C$_{1-4}$alkoxy, C$_{1-4}$haloalkyl (e.g., trifluoromethyl), —SH;
provided that when X, Y, or Z is nitrogen, R$_8$, R$_9$, or R$_{10}$, respectively, is not present;
(ii) R$_6$ is
H,
C$_{1-7}$alkyl,
C$_{3-7}$cycloalkyl (e.g., cyclopentyl or cyclohexyl),
aryl (e.g., phenyl),
heteroaryl (e.g., pyridyl, for example, pyrid-4-yl),
arylC$_{1-4}$alkyl (e.g., benzyl),
when L is a single bond, —N(H)—, —CH$_2$
wherein said aryl or heteroaryl is independently and optionally substituted with one or more halo (e.g., F, Cl), hydroxy, C$_{1-6}$alkyl, C$_{1-6}$alkoxy, C$_{3-8}$cycloalkyl, for example, R$_6$ is 4-hydroxyphenyl or 4-fluorophenyl
or R$_6$ is arylamino (e.g., phenylamino),
heterarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$),
when L is single bond or —CH$_2$—,
wherein the aryl or heteroaryl is optionally substituted with one or more halo (e.g., F, Cl), hydroxy, C$_{1-6}$alkyl, C$_{1-6}$alkoxy, C$_{3-8}$cycloalkyl, for example, R$_6$ is 4-hydroxyphenyl or 4-fluorophenyl,
and the rest of the substituents are as previously defined in Formula II, in free or salt form.

In still another embodiment, the invention provides a Compound of Formula II, wherein:
(i) Q is —C(=S)—;
(ii) R$_5$ is attached to one of the nitrogens on the pyrazolo portion of Formula II and is a moiety of Formula A

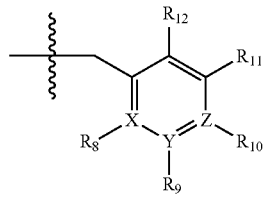

Formula A wherein X, Y and Z are, independently, N or C, and R$_8$, R$_9$, R$_{11}$ and R$_{12}$ are independently H or halogen (e.g., Cl or F), and R$_{10}$ is:
halogen,
C$_{1-4}$alkyl,
C$_{3-7}$cycloalkyl,
heteroC$_{3-7}$cycloalkyl (e.g., pyrrolidinyl or piperidinyl),
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl,
tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently and optionally substituted with one or more halo (e.g., F or Cl), C$_{1-4}$alkyl, C$_{1-4}$alkoxy, C$_{1-4}$haloalkyl (e.g., trifluoromethyl), —SH;
provided that when X, Y, or Z is nitrogen, R$_8$, R$_9$, or R$_{10}$, respectively, is not present;
(iii) R$_6$ is
H,
C$_{1-4}$alkyl,
C$_{3-7}$cycloalkyl (e.g., cyclopentyl or cyclohexyl),
aryl (e.g., phenyl),
heteroaryl (e.g., pyridyl, for example, pyrid-4-yl),
arylC$_{1-4}$alkyl (e.g., benzyl),
when L is a single bond, —N(H)—, —CH$_2$
wherein said aryl or heteroaryl is independently and optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl
or $R_6$ is
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$),
when L is single bond or —$CH_2$—,
wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl,
and the rest of the substituents are as previously defined in Formula II, in free or salt form.

In yet another embodiment, the invention provides a Compound of Formula II, wherein
(i) Q is —C(=S)—;
(ii) L is a single bond;
(iii) $R_5$ is attached to one of the nitrogens on the pyrazolo portion of Formula II and is a moiety of Formula A

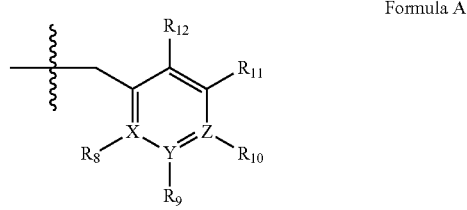

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl,
$C_{3-7}$cycloalkyl,
hetero$C_{3-7}$cycloalkyl (e.g., pyrrolidinyl or piperidinyl),
$C_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl,
tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocloalkyl is independently and optionally substituted with one or more halo (e.g., F or Cl), $C_{1-4}$alkyl, $C_{1-4}$alkoxy, $C_{1-4}$haloalkyl (e.g., trifluoromethyl), —SH;
provided that when X, Y, or Z is nitrogen, $R_8$, $R_9$, or $R_{10}$, respectively, is not present;
(iv) $R_6$ is —N($R_{18}$)($R_{19}$) and $R_{18}$ and $R_{19}$ are independently H,
$C_{1-4}$alkyl,
$C_{3-8}$cycloalkyl,
hetero$C_{3-8}$cycloalkyl,
aryl (e.g., phenyl) or
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, or
$C_{3-8}$cycloalkyl,
and the rest of the substituents are as previously defined in Formula II, in free or salt form.

In still another embodiment, the invention provides a Compound of Formula I or II wherein:
(i) Q is —C(=S)—;
(ii) L is a single bond;
(iii) $R_5$ is attached to one of the nitrogens on the pyrazolo portion of Formula I or II and is a moiety of Formula A

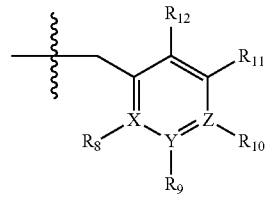

Formula A wherein X, Y and Z are, independently, N or C, and $R_8$, $R_9$, $R_{11}$ and $R_{12}$ are independently H or halogen (e.g., Cl or F), and $R_{10}$ is:
$C_{3-7}$cycloalkyl,
hetero$C_{3-7}$cycloalkyl (e.g., pyrrolidinyl or piperidinyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
wherein the aryl, heteroaryl, cycloalkyl, heterocloalkyl is independently and optionally substituted with one or more halo (e.g., F or Cl), $C_{1-4}$alkyl, $C_{1-4}$alkoxy, $C_{1-4}$haloalkyl (e.g., trifluoromethyl), —SH;
provided that when X, Y, or Z is nitrogen, $R_8$, $R_9$, or $R_{10}$, respectively, is not present;
(iv) $R_6$ is —N($R_{18}$)($R_{19}$) and $R_{18}$ and $R_{19}$ are independently H,
$C_{1-4}$alky,
aryl (e.g., phenyl),
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, or
$C_{3-8}$cycloalkyl,
and the rest of the substituents are as previously defined in Formula II, in free or salt form.

In yet another embodiment, the invention provides a compound selected from any of the following:
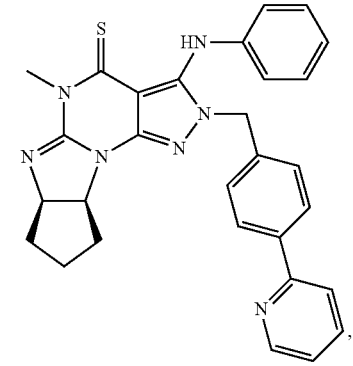
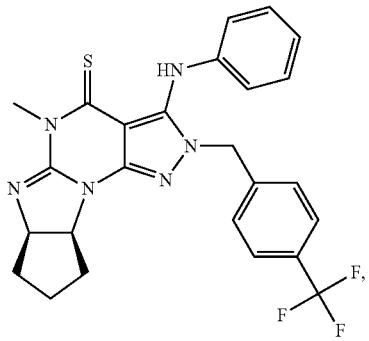
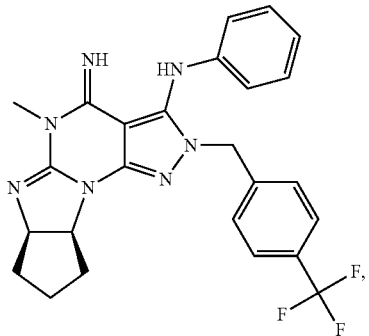
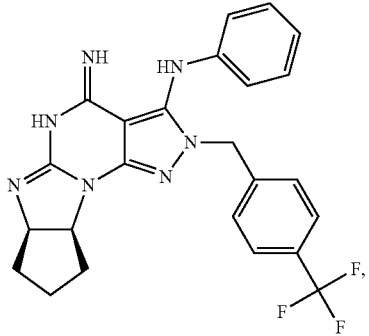
-continued
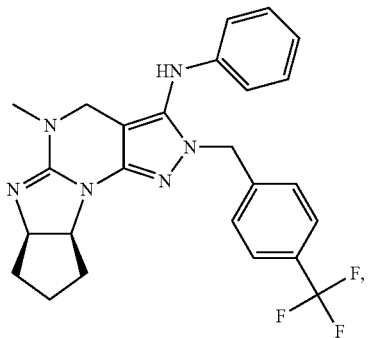
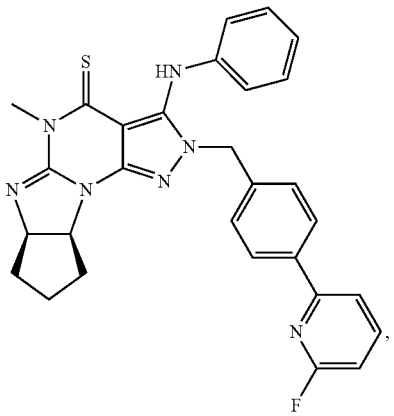
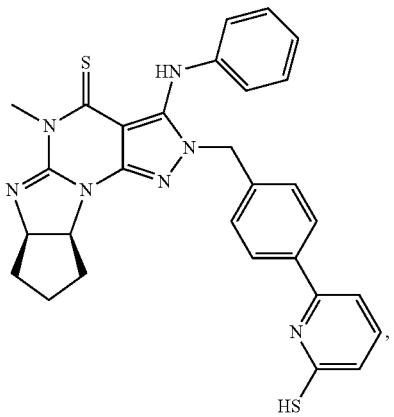
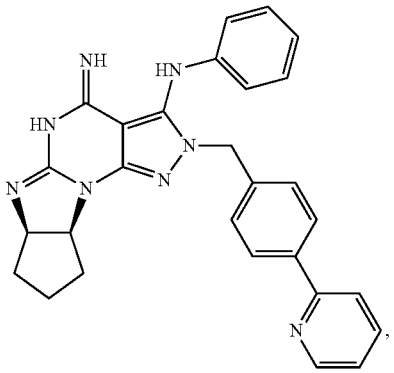

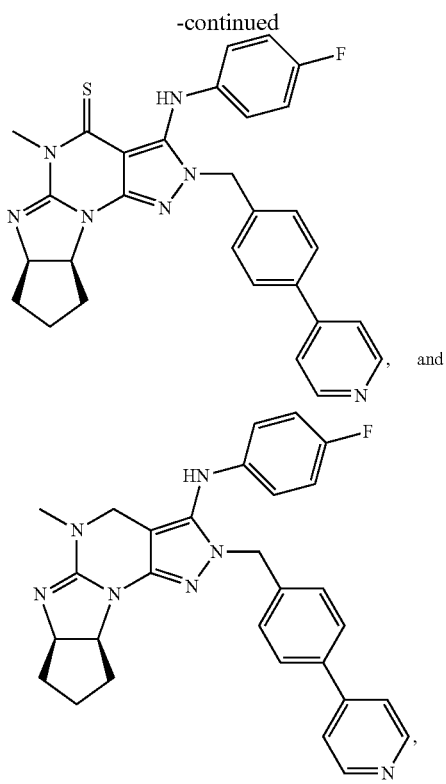

in free or salt form.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) Wherein E is phenylene, the numbering is as follows:

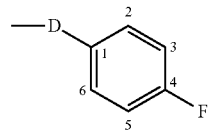

(g) It is intended that wherein the substituents end in "ene", for example, alkylene, phenylene or arylalkylene, said substitutents are intended to bridge or be connected to two other substituents. Therefore, methylene is intended to be —CH$_2$— and phenylene intended to be —C$_6$H$_4$— and arylalkylene is intended to be —C$_6$H$_4$—CH$_2$— or —CH$_2$—C$_6$H$_4$—.

(h) The Compounds of the Invention are intended to be numbered as follows:

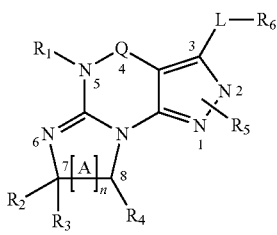

Compounds of the Invention, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula I, e.g., any of formulae 1.1-1.80, or Compound of Formula II as described herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction), or a disease or disorder such as psychosis or glaucoma). This list is not intended to be exhaustive and may include other diseases and disorders as set forth below.

In another embodiment, the invention further provides a pharmaceutical composition comprising a Compound of the Invention, in free, pharmaceutically acceptable salt or prodrug form, in admixture with a pharmaceutically acceptable carrier.

DETAILED DESCRIPTION OF THE INVENTION

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. Various starting materials and/or Compounds of the Invention may be prepared using methods described in WO 2006/133261 and PCT/US2007/070551. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-raradioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

TERMS AND ABBREVIATIONS

BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
$Et_2O$=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
$NaHCO_3$=sodium bicarbonate,
$NH_4OH$=ammonium hydroxide,
$Pd_2(dba)_3$=tris[dibenzylideneacetone]dipalladium(0)
PMB=p-methoxybenzyl,
$POCl_3$=phosphorous oxychloride,
$SOCl_2$=thionyl chloride,
TFA=trifluoroacetic acid,
TFMSA=trifluoromethanesulfonic acid
THF=tetrahedrofuran.

The synthetic methods in this invention are illustrated below. The significances for the R groups are as set forth above for formula I or II unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled.

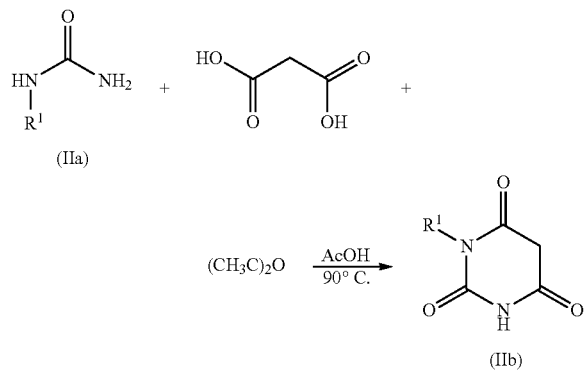

(IIa)

(IIb)

wherein R¹ is methyl.

Intermediate IIc can be prepared by for example reacting a compound of III) with for example a chlorinating compound such as POCl₃, sometimes with small amounts of water and heated for about 4 hours and then cooled

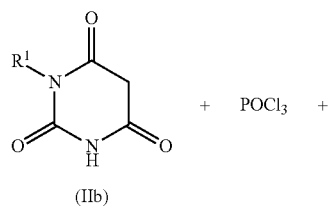

(IIb)

(IIc)

Intermediate IId may be formed by reacting a compound of IIc with for example a P¹-L in a solvent such as DMF and a base such as K₂CO₃ at room temperature or with heating:

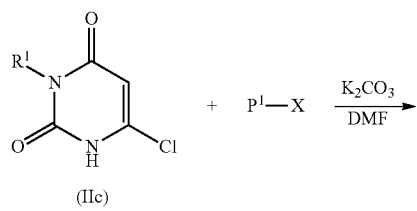

(IIc)

(IId)

wherein $P_1$ is a protective group [e.g., p-methoxybenzyl group (PMB)]; X is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

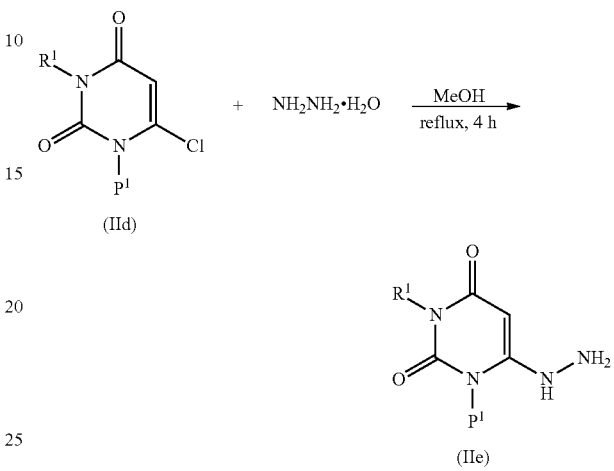

(IId)

(IIe)

Intermediate IIf can be synthesized by reacting a compound of IIc with hydrazine or hydrazine hydrate in a solvent such as methoxyethanol and refluxed for about 30 min and then cooled:

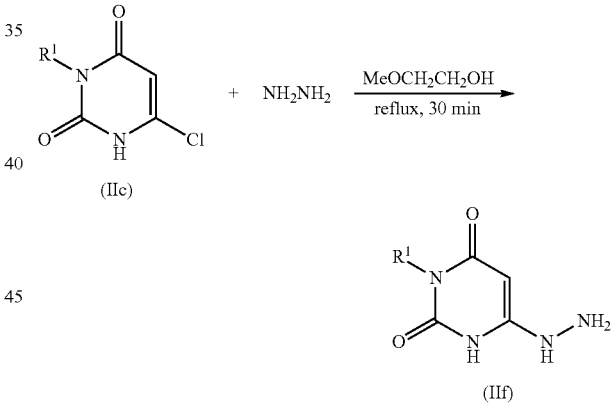

(IIc)

(IIf)

Intermediate IIg (wherein L is —NH— and $R_6$ is for example an aryl group), can be synthesized by reacting a compound of IIe with for example an aryl isothiocyanate or isocyanate in a solvent such as DMF and heated at 110° C. for about 2 days and then cooled:

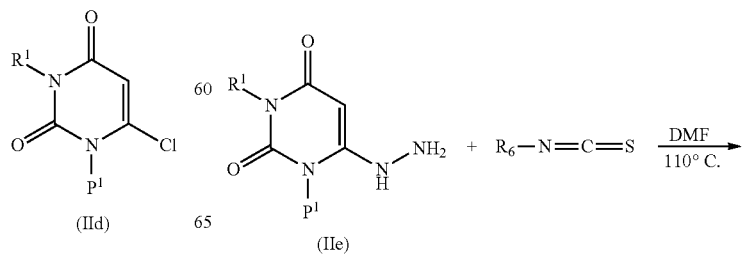

(IIe)

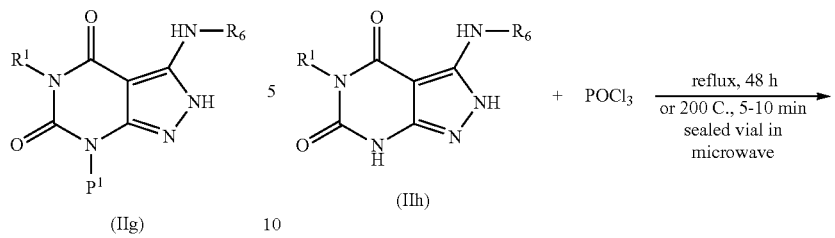

Intermediate IIh may be synthesized from a compound of IIg by removing the protective group $P^1$ with an appropriate method. For example, if $P^1$ is a p-methoxybenzyl group, then it can be removed with $AlCl_3$ at room temperature or with TFA under heated conditions.

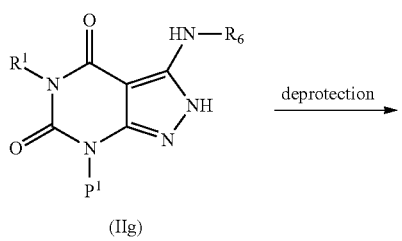

Intermediate IIh may also be prepared directly from a compound of IIf using the similar methods, but the yields are relatively low.

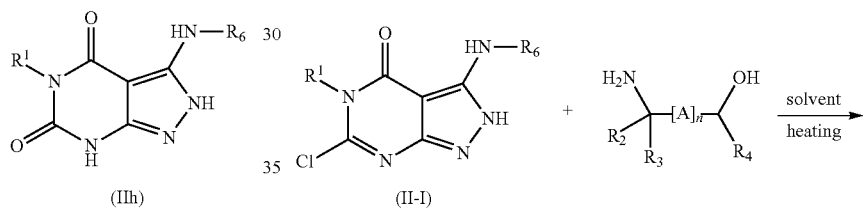

Intermediate II-I can be prepared by for example reacting a compound of IIh with for example a chlorinating compound such as $POCl_3$. The reaction may be carried out at atmospheric pressure and refluxed for about 2 days, or heated at 150–200° C. for about 10 min in a sealed vial with a microwave instrument.

Intermediate IIJ can be prepared by reacting a compound of II-I with an amino alcohol in a solvent such as DMF. The reaction may be heated overnight and then cooled. The reaction mixture may be purified by chromatography to obtain compound IIJ:

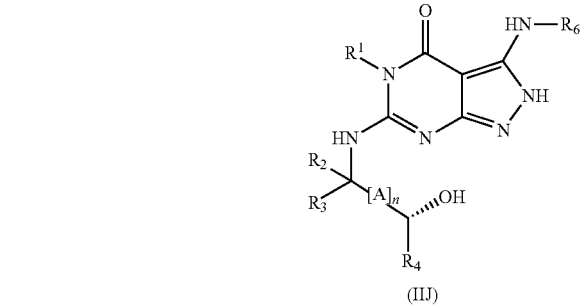

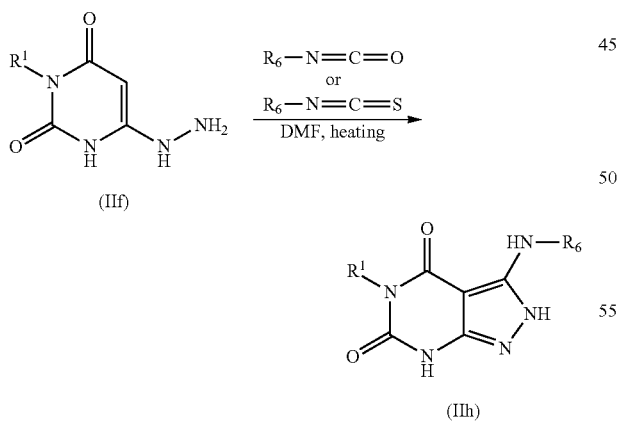

wherein all the substituents are as defined previously in Formula I or II. For example, the amino alcohol may be 1-amino-2-cyclopentanol:

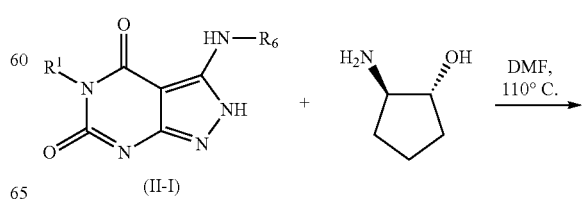

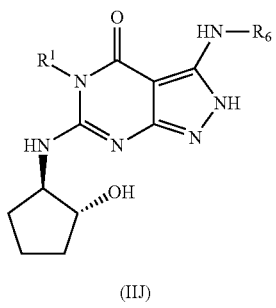

(IIJ)

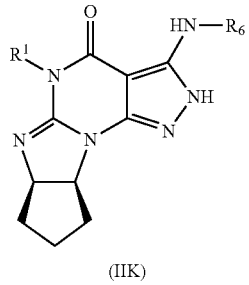

(IIK)

Intermediate IIK can be formed by reacting a compound of IIJ with for example a dehydrating/halogenating agent such as SOCl$_2$ in a solvent such as CH$_2$Cl$_2$ at room temperature overnight or heated at 35° C. for several hours, and then cooled to obtain cyclized compound (IIK).

Compound Ia and Ib may be formed by reacting a compound of IIk with for example a R$_5$—X in a solvent such as DMF and a base such as K$_2$CO$_3$ at room temperature or with heating:

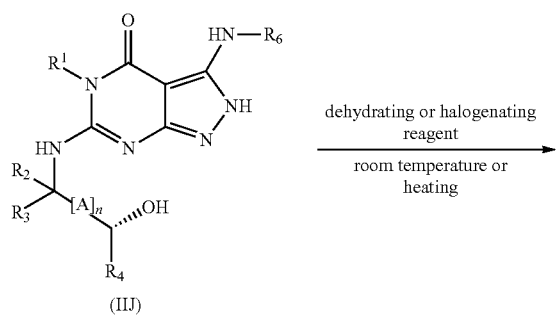

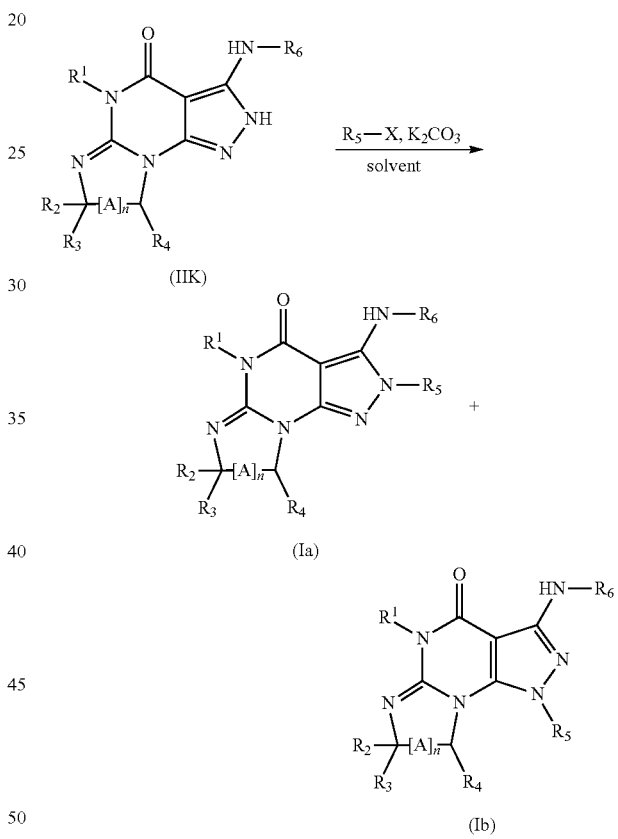

For Example:

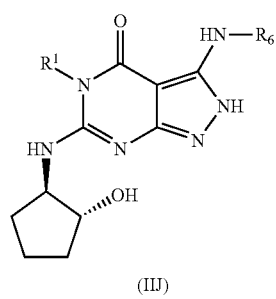

For example:

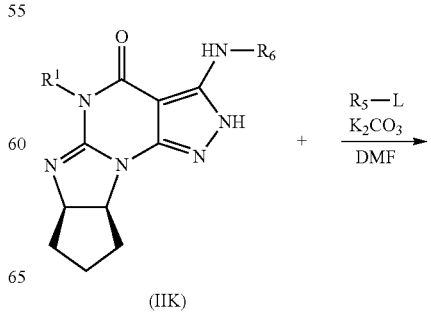

-continued

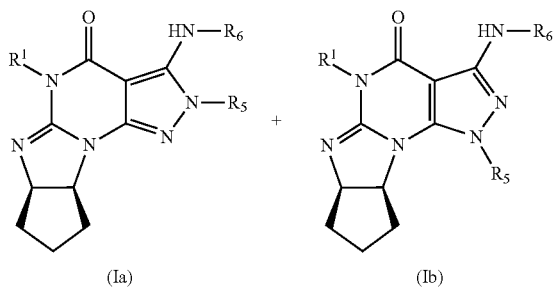

(Ia)  (Ib)

wherein all the substituents are as defined previously; X is a leaving group such as a halogen, mesylate, or tosylate.

$R_5$ may also be introduced earlier by for example reacting IIg with $R_5$—X and then perform similar procedure as described above to form compound Ia and Ib, as long as $R_5$ will not be cleaved off in the $P^1$ deprotection step.

The third synthetic route is also developed for the preparation of Compound Ia.

Intermediate IVa may be formed by for example reacting a compound of IIe with $POCl_3$ and DMF:

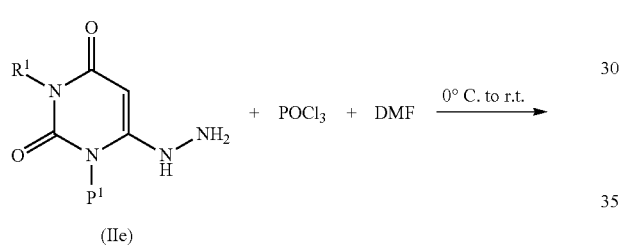

(IIe)

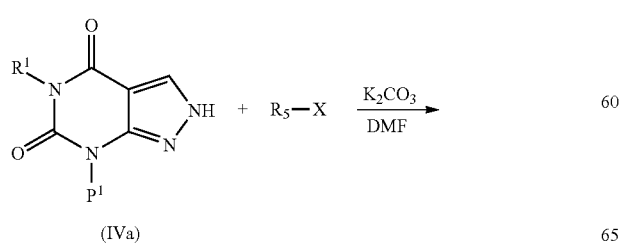

(IVa)

wherein $R^1$ is as defined previously, such as a methyl group.

Intermediate IVb may be formed by reacting a compound of IVa with for example a $R_5$—X in a solvent such as DMF and a base such as $K_2CO_3$ at room temperature or with heating:

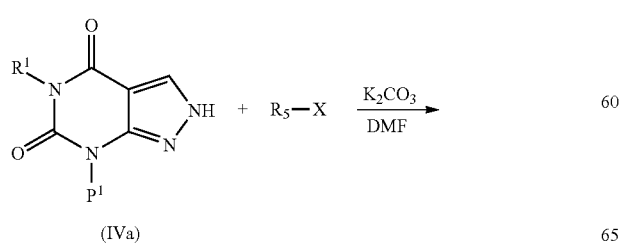

(IVa)

-continued

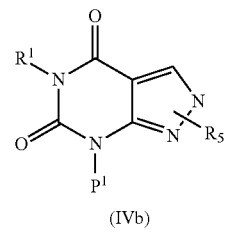

(IVb)

Intermediate IVc may be synthesized from a compound of IVb by removing the protective group $P^1$ with an appropriate method. For example, if $P^1$ is a PMB group, then it can be removed with CAN or TFA/TFMSA at room temperature:

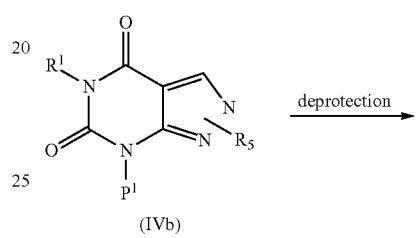

(IVb)

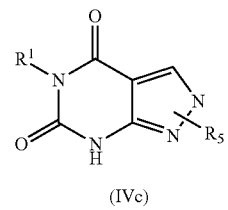

(IVc)

Intermediate IVd can be prepared by reacting a compound of IVc with for example a chlorinating compound such as $POCl_3$ and refluxed for about 2 days, or heated at 150-200° C. for about 10 min in a sealed vial with a microwave instrument and then cooled:

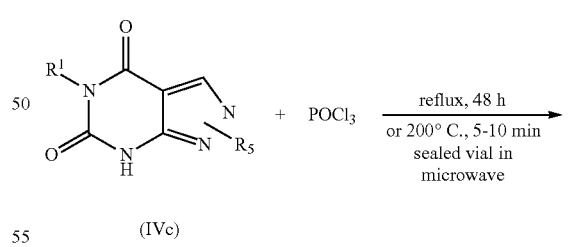

(IVc)

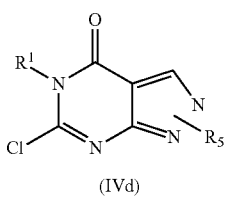

(IVd)

Intermediate IVe can be formed by reacting a compound of IVd with an amino alcohol under basic condition in a solvent such as DMF and heated overnight then cooled:

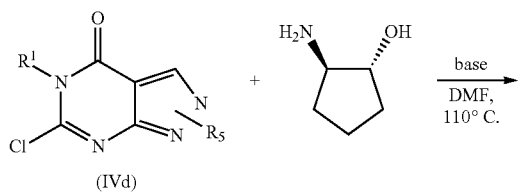

wherein all the substituents are as defined previously in Formula I or II.

Compound IVf may be formed by reacting a compound of IVe with for example a dehydrating/halogenating agent such as SOCl$_2$ in a solvent such as CH$_2$Cl$_2$ at room temperature overnight or heated at 35° C. for several hours, and then cooled.

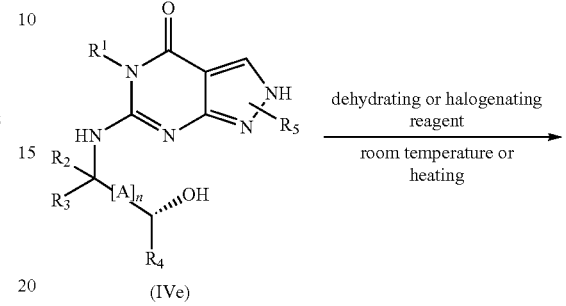

Alternatively, intermediate IVe can be synthesized directly from a compound of IVc by reacting with an amino alcohol and a coupling reagent such as BOP in the presence of a base such as DBU:

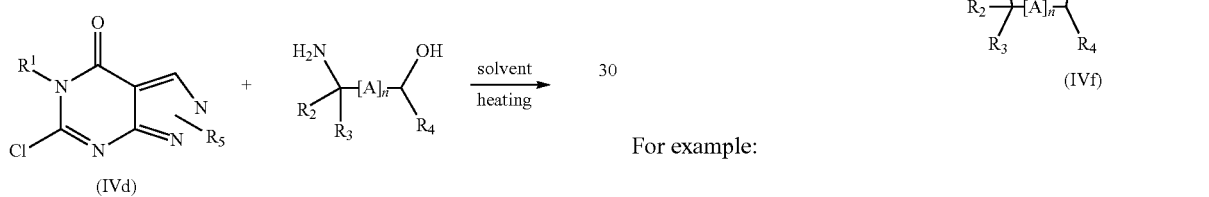

For example:

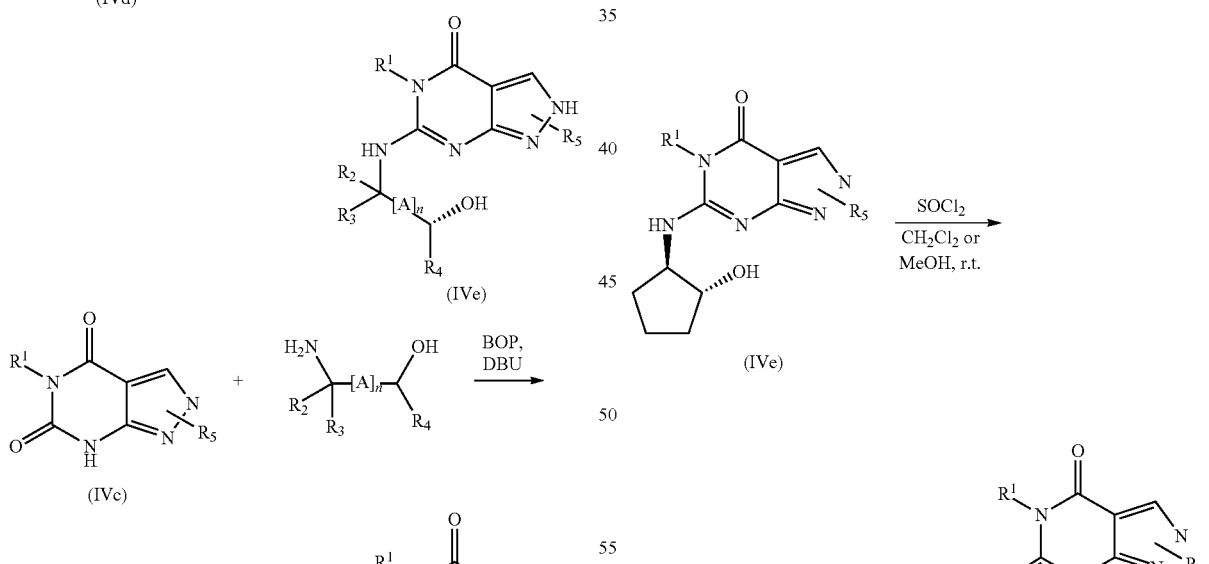

Compound IVg may be formed by reacting a compound of IVf with for example a halogenating agent such as hexachloroethane and a base such as LiHMDS in a solvent such as THF at low temperature.

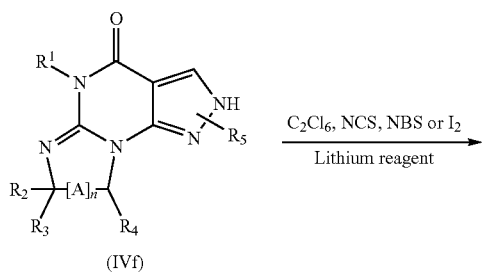

(IVf)

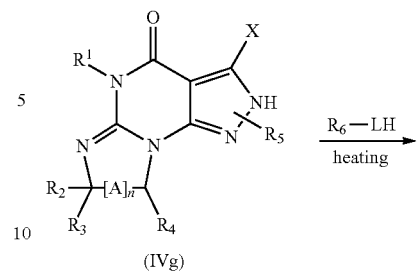

(IVg)

For example:

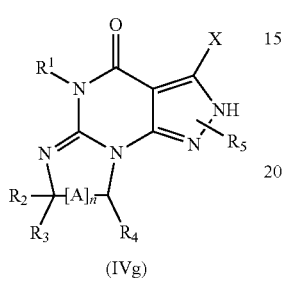

(IVg)

For example, a compound of formula IVg reacting with an aniline in the present of a catalyst such as $Pd_2(dba)_3$ in a solvent such as dioxane at 100° C. overnight to give a Compound Ia.

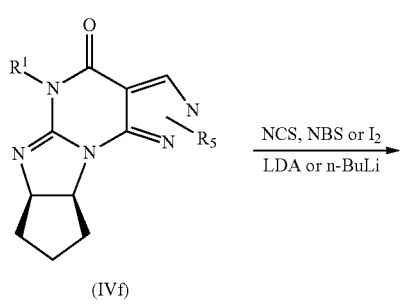

(IVf)

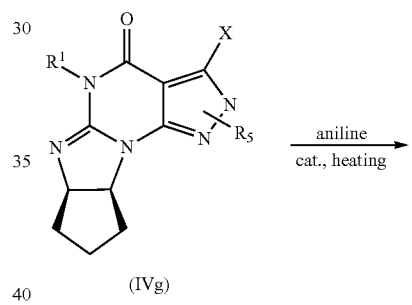

(IVg)

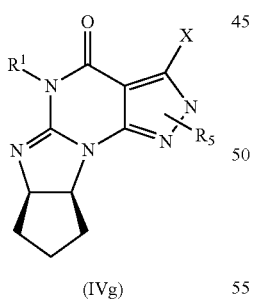

(IVg)

Compound Ia may be formed by reacting a compound of IVg with for example an amine upon heating. If $R_6$-LH is an aryl amine, a catalyst may be required to facilitate the reaction or a strong base such as LiHMDS may be used to accelerate the reaction.

Compound Ia where in L=$CH_2$ may be prepared using the general synthetic methods described in Example 3 of U.S. Patent Publication No. 2008/0188492 (or WO 2006/133261), the contents of which are incorporated by reference in their entirety). For example, wherein L is a —$CH_2$— and $R_6$ is aryl (e.g., -L-$R_6$ is benzyl), the compound may be prepared by reacting, e.g., 4-phenylbenzaldehyde with 6-hydrazinyl-1-(4-methoxybenzyl)-3-methylpyrimidine-2,4(1H,3H)-dione to produce 6-(2-(Biphenyl-4-ylmethylene)hydrazinyl)-1-(4-methoxybenzyl)-3-methylpyrimidine-2,4(1H,3H)-dione. The resulting compound can then react with 2-phenylacetaldehyde in the presence of, e.g., piperidine at elevated temperature, e.g., 40-45 degrees C. in a solvent such as DMF and $Bu^tOH$, to give 3-Benzyl-2-(biphenyl-4-ylmethyl)-7-(4- methoxybenzyl)-5-methyl-2H-pyrazolo[3,4-d]pyrimidine-4,6(5H,7H)-dione, which is then reacted with ammonium cerium (IV) nitrate to give 3-Benzyl-2-(biphenyl-4-ylmethyl)-5-methyl-2H-pyrazolo[3,4-d]pyrimidine-4,6(5H,7H)-dione:

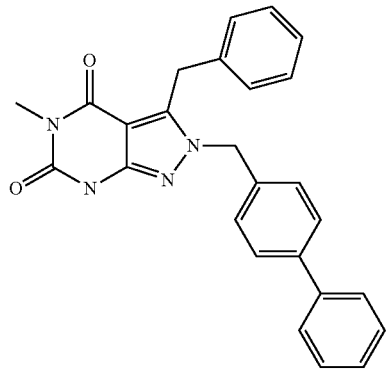 [SMILES: Cn1c(=O)[nH]c2nn(Cc3ccc(-c4ccccc4)cc3)c(Cc3ccccc3)c2c1=O]

This resulting dione compound can then be reacted with an amino alcohol and a coupling reagent such as BOP in the presence of a base such as DBU to obtain a compound of Formula I or II, wherein L is —CH$_2$—, R$_6$ is phenyl and R$_5$ is phenyl-4-ylmethyl. Alternatively, wherein R$_5$ is a pyridyl-phenyl-methyl, 4-pyridylbenzaldehyde may be used instead of 4-phenylbenzaldehyde.

Compound of the Invention wherein Q is CH$_2$ may be prepared by reacting Compound (Ia) with a reducing agent, e.g., DIBAL-H, LAH, preferably DIBAL-H.

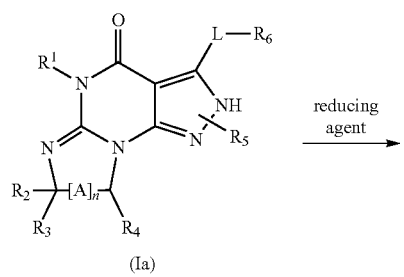

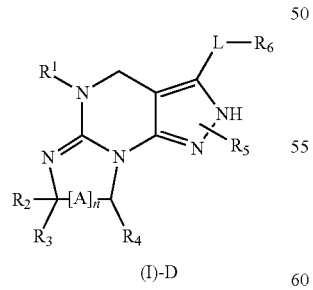

Compound of the Invention wherein Q is C(═S) may be prepared by reacting Compound (Ia) with P$_4$S$_{10}$ in the presence of a base, e.g., pyridine.

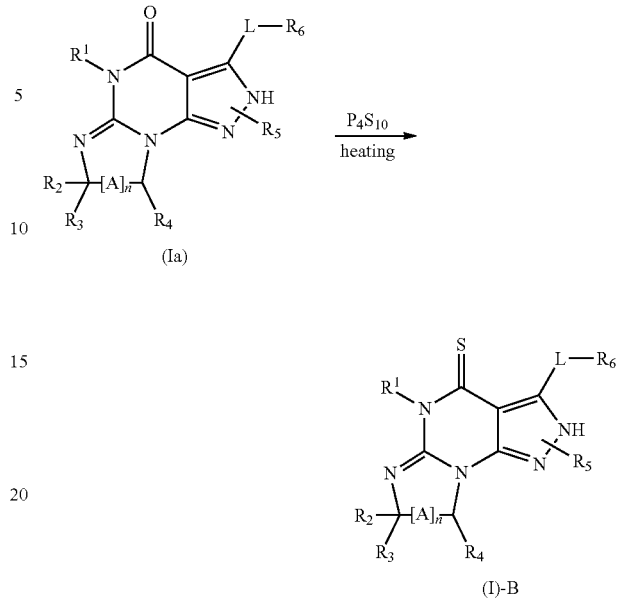

Compound of the Invention wherein Q is C(═N(R$_{20}$)) may be prepared by reacting compound (I)-B with NH$_2$(R$_{20}$) in the presence of HgCl$_2$ upon heating.

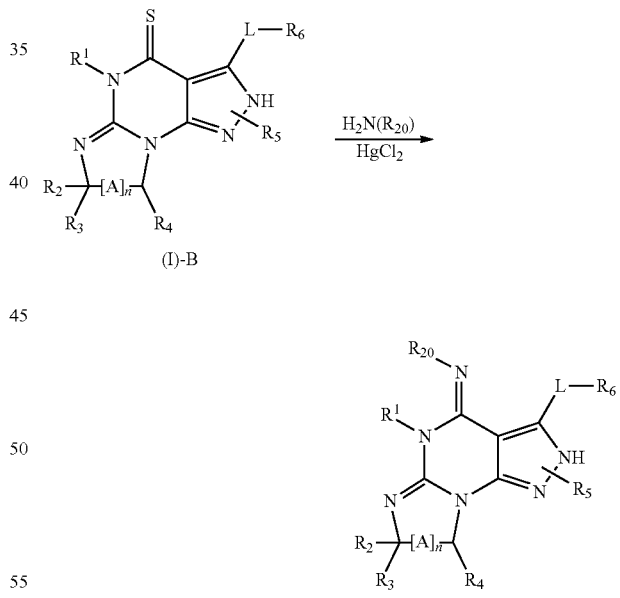

In another aspect of the invention, The invention thus provides methods of making Compounds of Formula I, for example, comprising reacting Compounds I-A with, for example, R$_5$—X, in a solvent such as DMF and a base such as K$_2$CO$_3$ at room temperature or with heating:

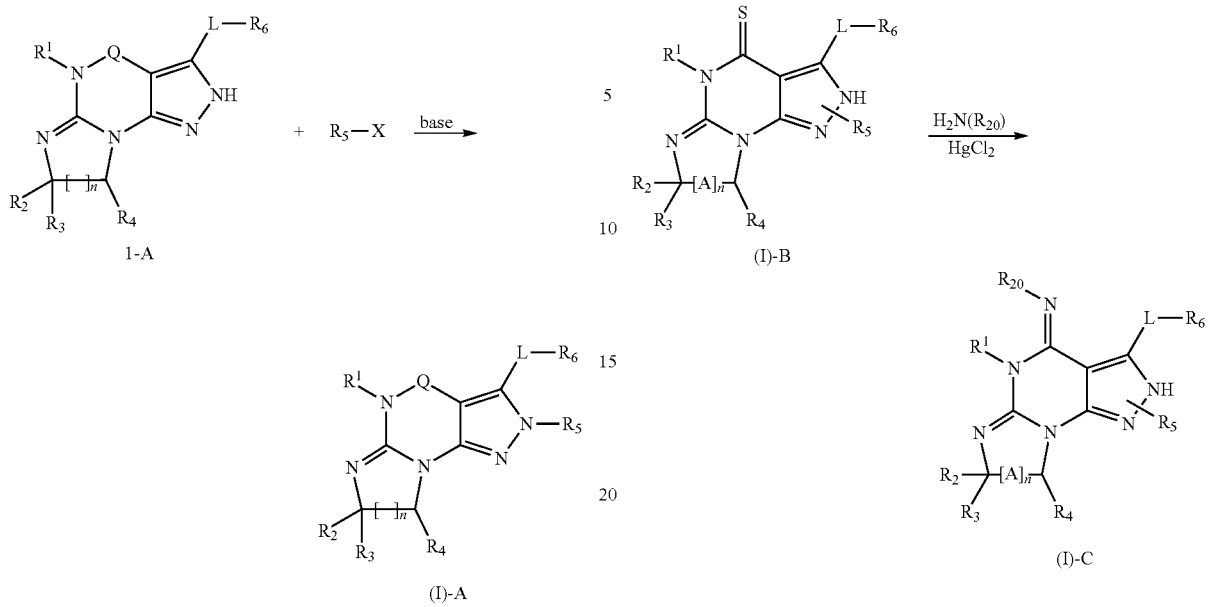

1-A wherein all the substitutents are as defined previously; X is a leaving group such as a halogen, mesylate, or tosylate.

The thione compounds of the invention, e.g., Compounds of Formula I or II wherein Q is C(=S) or (I)-B may then be prepared by reacting Compound (Ia) with $P_4S_{10}$ in a microwave vial in the presence of a base, e.g., pyridine, and heating the mixture to an elevated temperature, e.g., in a microwave, e.g., to about 150° C.

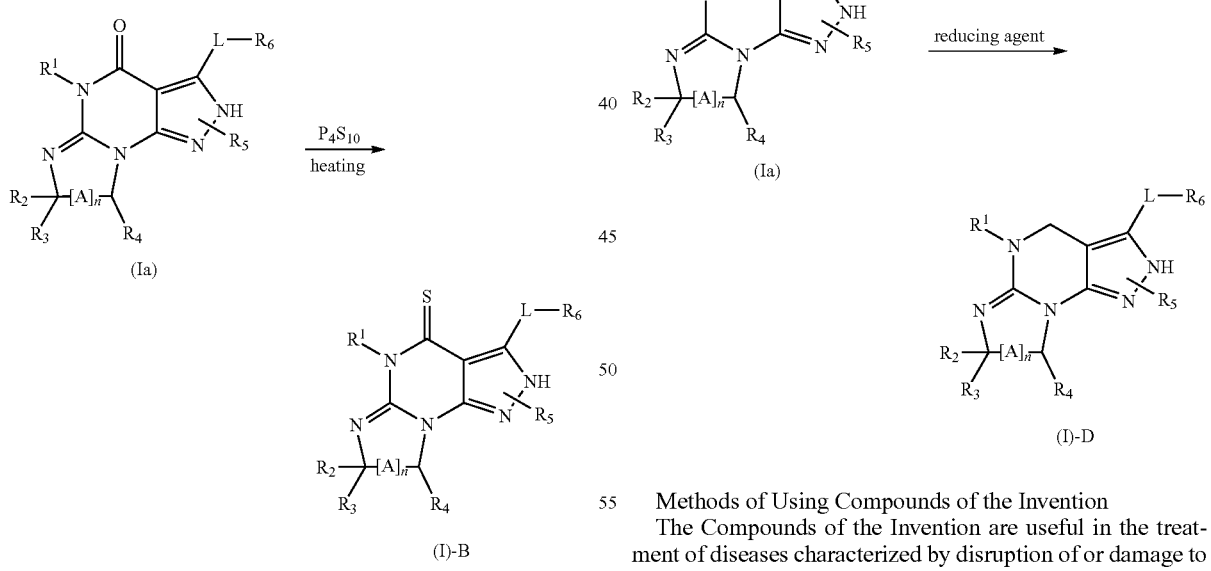

The imine compounds of the Invention, e.g., Compounds of Formula I or II wherein Q is C(=N($R_{20}$)) or (I)-C may in turn be converted from the thione derivative (i.e., Compounds of Formula (I) wherein with Q is X(=S) or (I)-B by reacting the thione derivative with $NH_2(R_{20})$ in the presence of $HgCl_2$, e.g., in a solvent such as THF, and heating the reaction mixture to an elevated temperature, e.g., in a microwave, e.g., to about 110° C.

The Compounds of the Invention, e.g., Compounds of Formula (I) wherein Q is $CH_2$, Compound (I)-D, may also be prepared by reacting the ketone derivative, e.g., Formula I wherein Q is C(=O) or Compound (I)-A, with a reducing agent, e.g., diisobutylaluminum hydride (DIBAL-H), lithium aluminum hydride, sodium borohydride, preferably, DIBAL-H.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, and sexual dysfunction;

(iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., a compound according to any of Formula I or 1.1-1.80, in free, pharmaceutically acceptable salt or prodrug form, to a human or animal patient in need thereof. In another aspect, the invention provides a method of treatment of the conditions disclosed above comprising administering a therapeutically effective amount of a Compound of Formula II as hereinbefore described, in free or pharmaceutically acceptable salt form, to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE 1 Inhibitor, e.g., a compound according to any of Formula I or any of 1.1-1.80, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

in free, pharmaceutically acceptable salt or prodrug form, to a human or animal patient in need thereof. In still another embodiment, the methods of treatment or prophylaxis for narcolepsy as hereinbefore described, comprises administering a therapeutically effective amount of a Compound of Formula II as hereinbefore described, in free or pharmaceutically acceptable salt form, as a sole therapeutic agent or use in combination for co-administered with another active agent.

In another embodiment, the invention further provides methods of treatment or prophylaxis of a condition which may be alleviated by the enhancement of the progesterone signaling comprising administering an effective amount of a Compound of the Invention, e.g., a compound according to any of Formula I or any of 1.1-1.80, in free, pharmaceutically acceptable salt or prodrug form, to a human or animal patient in need thereof. The invention also provides methods of treatment as disclosed here, comprising administering a therapeutically effective amount of a Compound of Formula II, in free or pharmaceutically acceptable salt form. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., a compound according to any of Formula I or any of 1.1-1.80, and (ii) a hormone, e.g., selected from estrogen and estrogen analogues (e.g., estradiol, estriol, estradiol esters) and progesterone and progesterone analogues (e.g., progestins)

in free, pharmaceutically acceptable salt or prodrug form, to a human or animal patient in need thereof. In another embodiment, the invention provides the method described above wherein the PDE 1 inhibitor is a Compound of Formula II, in free or pharmaceutically acceptable salt form.

The invention also provides a method for enhancing or potentiating dopamine D1 intracellular signaling activity in a cell or tissue comprising contacting said cell or tissue with an amount of a Compound of the Invention, e.g., Formula I or any of 1.1-1.80, sufficient to inhibit PDE1B activity. The invention further provides a method for enhancing or potentiating dopamine D1 intracellular signaling activity in a cell or tissue comprising contacting said cell or tissue with an amount of a Compound of Formula II as hereinbefore described, in free or salt form, sufficient to inhibit PDE1 activity, e.g., PDE1A or PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., Formula I or any of 1.1-1.80, in that inhibits PDE1B, wherein PDE1B activity modulates phosphorylation of DARPP-32 and/or the GluR1 AMPA receptor. Similarly, the invention provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of Formula II as hereinbefore described, in free or pharmaceutically acceptable salt form.

In another aspect, the invention also provides a method for the treatment for glaucoma or elevated intraocular pressure comprising topical administration of a therapeutically effective amount of a phosphodiesterase type I (PDE1) Inhibitor of the Invention, in free or pharmaceutically acceptable salt form, in an opthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, in free or ophthamalogically acceptable salt form, in combination or association with an ophthamologically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, in free or pharmaceutically acceptable salt form, such that amount of the agent known to lower intraocular pressure and the amount of the PDE1 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE-1 Inhibitor of the Invention together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE 1 inhibitor may be administered in the form of an ophthalmic composition, which includes an ophthalmic solution, cream or ointment. The ophthalmic composition may additionally include an intraocular-pressure lowering agent.

In yet another example, the PDE-1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously administering therapeutically effective amounts of:
   (i) a PDE 1 Inhibitor of the invention, in free or pharmaceutically acceptable salt form; and
   (ii) an antipsychotic, e.g.,
      Typical antipsychotics, e.g.,
         Butyrophenones, e.g. Haloperidol (Haldol, Serenace), properidol (Droleptan);
         Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
         Thioxanthenes, e.g., Chlorprothixene, Flupenthixol (Depixol, Fluanxol), Thiothixene (Navane), Zuclopenthixol (Clopixol, Acuphase);
      Atypical antipsychotics, e.g.,
         Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 inhibitor of the invention, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter. For a review of TBI, see Park et al., CMAJ (2008) 178(9):1163-1170, the contents of which are incorporated herein in their entirety. Studies have shown that the cAMP-PKA signaling cascade is downregulated after TBI and treatment of PDE IV inhibitors such as rolipram to raise or restore cAMP level improves histopathological outcome and decreases inflammation after TBI. As Compounds of the present invention is a PDE1 inhibitor, it is believed that these compounds are also useful for the treatment of TBI, e.g., by restoring cAMP level and/or calcium homeostasis after traumatic brain injury.

The present invention also provides
   (i) a Compound of the Invention, e.g., Formula I or any of 1.1-1.80, or Formula II as hereinbefore described, in free, pharmaceutically acceptable salt or prodrug form for example for use in any method or in the treatment of any disease or condition as hereinbefore set forth,
   (ii) the use of a Compound of the Invention, e.g., Formula I or any of 1.1-1.80, or Formula II as hereinbefore described, in free, pharmaceutically acceptable salt or prodrug form, in the manufacture of a medicament for treating any disease or condition as hereinbefore set forth,
   (iii) a pharmaceutical composition comprising a Compound of the Invention, e.g., Formula I or any of 1.1-1.80, or Formula II as hereinbefore described, in free, pharmaceutically acceptable salt or prodrug form, in combination or association with a pharmaceutically acceptable diluent or carrier, and
   (iv) a pharmaceutical composition comprising a Compound of the Invention, e.g., Formula I or any of 1.1-1.80, or Formula II as hereinbefore described, in free, pharmaceutically acceptable salt or prodrug form, in combination or association with a pharmaceutically acceptable diluent or carrier for use in the treatment of any disease or condition as hereinbefore set forth.

Therefore, the invention provides use of a Compound of the Invention, e.g., Formula I or any of 1.1-1.80, or Formula II as hereinbefore described, in free, pharmaceutically acceptable salt or prodrug form, or a Compound of the Invention in a pharmaceutical composition form, for the manufacture of a medicament for the treatment or prophylactic treatment of the following diseases: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, for the manufacture of a medicament for the treatment or prophylactic treatment of:
a) glaucoma or elevated intraocular pressure,
b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder, or
c) traumatic brain injury.

The phrase "Compounds of the Invention" or "PDE 1 inhibitors of the Invention" encompasses any and all of the compounds disclosed herewith, e.g., a Compound of Formula I or any of 1.1-1.80 and Formula II.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "pulmonary hypertension" is intended to encompass pulmonary arterial hypertension.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy and female sexual dysfunction.

Compounds of the Invention, e.g., Formula I or any of 1.1-1.80, or Formula II as hereinbefore described, in free or pharmaceutically acceptable salt form, may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The synthetic methods for various Compounds of the Present Invention are illustrated below. Other compounds of the Invention and their salts may be made using the methods as similarly described below and/or by methods similar to those generally described in the detailed description and by methods known in the chemical art.

Example 1

(6aR,9aS)-2,4,5,6a,7,8,9,9a-octahydro-5-methyl-3-(phenylamino)-2-((4-Pyridin-2-yl)-benzyl)-cyclopent[4,5]imidazo[1,2-a]pyrazolo[4,3-e]pyrimidine

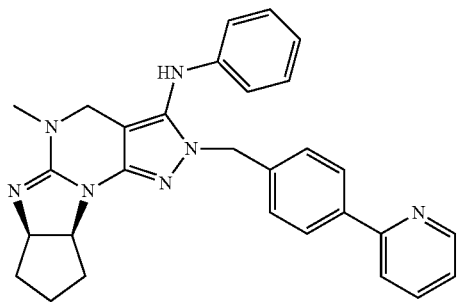 [SMILES: CN1Cc2c(nn(Cc3ccc(-c4ccccn4)cc3)c2Nc2ccccc2)N2C1=N[C@@H]1CCC[C@@H]12]

(6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-one (26.9 mg, 0.055 mmol) is dissolved in 1 mL of anhydrous THF, and then 400 uL of 1.5 M DIBAL-H in toluene is added dropwise. After the reaction mixture is stirred at room temperature overnight, additional 800 uL of 1.5 M DIBAL-H is added to the solution.

The reaction mixture is stirred at room temperature for 24 hours, and then quenched with NH₄Cl aqueous solution. After routine workup, the mixture is purified by a semi-preparative HPLC to give 3.0 mg of pure product as while solids. MS (ESI) m/z 476.3 [M+H]⁺.

Example 2

(6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-thione

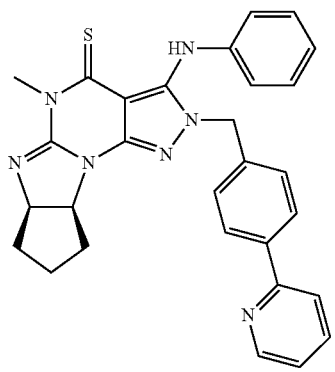 [SMILES: CN1C(=S)c2c(nn(Cc3ccc(-c4ccccn4)cc3)c2Nc2ccccc2)N2C1=N[C@@H]1CCC[C@@H]12]

(6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-one (36.1 mg, 0.055 mmol) and $P_4S_{10}$ are placed in a Biotage microwave vial, and then 1 mL of pyridine is added. The reaction mixture is heated in a microwave at 150° C. for 2.5 h. Pyridine is removed under high vacuum. The obtained crude product is purified by a semi-preparative HPLC to give 3.2 mg of pure product as pale yellow solids. MS (ESI) m/z 506.2 [M+H]⁺.

Example 3

(6aR,9aS)-5,6a,7,8,9,9a-hexahydro-5-methyl-3-(phenylamino)-2-(4-trifluoromethyl-benzyl)-cyclopent[4,5]imidazo[1,2-a]pyrazolo[4,3-e]pyrimidin-4(2H)-thione

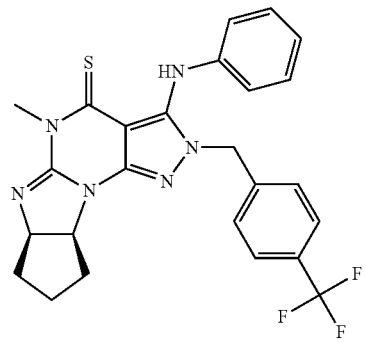 [SMILES: CN1C(=S)c2c(nn(Cc3ccc(C(F)(F)F)cc3)c2Nc2ccccc2)N2C1=N[C@@H]1CCC[C@@H]12]

(6aR,9aS)-5,6a,7,8,9,9a-hexahydro-5-methyl-3-(phenylamino)-2-((4-trifluoromethyl-benzyl)-cyclopent[4,5]imidazo[1,2-a]pyrazolo[4,3-e]pyrimidin-4(2H)-one (100 mg, 0.21 mmol) and $P_4S_{10}$ (159 mg, 0.36 mmol) are placed in a Biotage microwave vial, and then 3 mL of dioxane is added. The reaction mixture is heated in a microwave at 150° C. for 3 h. Solvent is removed under high vacuum. The obtained crude product is purified by a semi-preparative HPLC to give 61 mg of pure product as pale yellow solids (yield: 59%). MS (ESI) m/z 497.2 [M+H]⁺.

Example 4

(6aR,9aS)-2,5,6a,7,8,9,9a-heptahydro-4-imino-5-methyl-3-(phenylamino)-2-(4-trifluoromethyl-benzyl)-cyclopent[4,5]imidazo[1,2-a]pyrazolo[4,3-e]pyrimidine

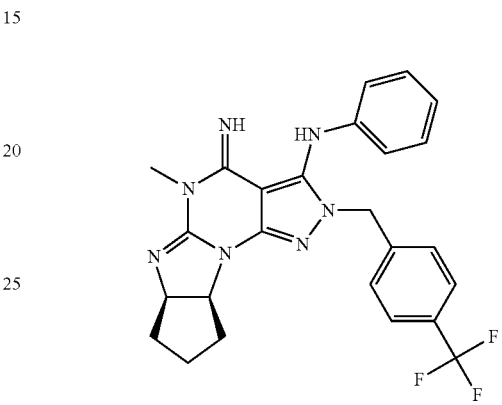

(6aR,9aS)-5,6a,7,8,9,9a-hexahydro-5-methyl-3-(phenylamino)-2-((4-trifluoromethyl-benzyl)-cyclopent[4,5]imidazo[1,2-a]pyrazolo[4,3-e]pyrimidin-4(2H)-thione (18.2 mg, 0.037 mmol) and HgCl₂ (20.1 mg, 0.074 mmol) are placed in a Biotage microwave vial, and then 0.5 mL of 7N ammonia in methanol is added. The reaction mixture is heated in a microwave at 110° C. for 3 h, and then filtered to remove solids. The obtained filtrate is evaporated to dryness, and then purified by a semi-preparative HPLC to give 7.0 mg of pure product as white solids. MS (ESI) m/z 480.2 [M+H]⁺.

Example 5

(6aR,9aS)-2,5,6a,7,8,9,9a-heptahydro-4-imino-3-(phenylamino)-2-(4-trifluoromethyl-benzyl)-cyclopent[4,5]imidazo[1,2-a]pyrazolo[4,3-e]pyrimidine

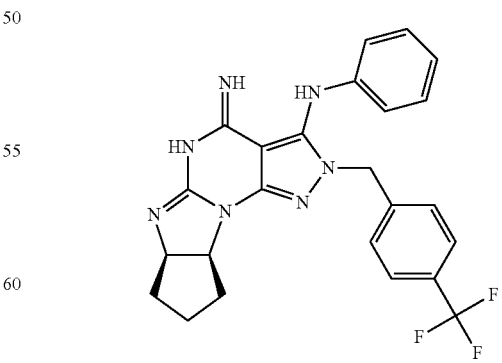

The synthetic procedure of this compound is the same as EXAMPLE 4. (6aR,9aS)-2,5,6a,7,8,9,9a-heptahydro-4-imino-3-(phenylamino)-2-(4-trifluoromethyl-benzyl)-cyclopent[4,5]imidazo[1,2-a]pyrazolo[4,3-e]pyrimidine (5.0 mg) is obtained as a minor product (white solid). MS (ESI) m/z 466.2 [M+H]⁺.

Example 6

(6aR,9aS)-2,4,5,6a,7,8,9,9a-octahydro-5-methyl-3-(phenylamino)-2-(4-trifluoromethyl-benzyl)-cyclopent[4,5]imidazo[1,2-a]pyrazolo[4,3-e]pyrimidine

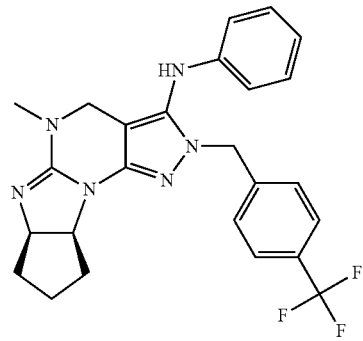 [SMILES: CN1Cc2c(nn(Cc3ccc(C(F)(F)F)cc3)c2Nc2ccccc2)N2C1=N[C@@H]1CCC[C@@H]12]

The synthetic procedure of this compound is analogous to EXAMPLE 1 wherein (6aR,9aS)-5,6a,7,8,9,9a-hexahydro-5-methyl-3-(phenylamino)-2-((4-trifluoromethyl-benzyl)-cyclopent[4,5]imidazo[1,2-a]pyrazolo[4,3-e]pyrimidin-4(2H)-one is used instead of (6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-one. MS (ESI) m/z 467.2 [M+H]⁺.

Example 7

(6aR,9aS)-5,6a,7,8,9,9a-hexahydro-5-methyl-3-(phenylamino)-2-(4-(6-fluoropyridin-2-yl)-benzyl)-cyclopent[4,5]imidazo[1,2-a]pyrazolo[4,3-e]pyrimidin-4(2H)-thione

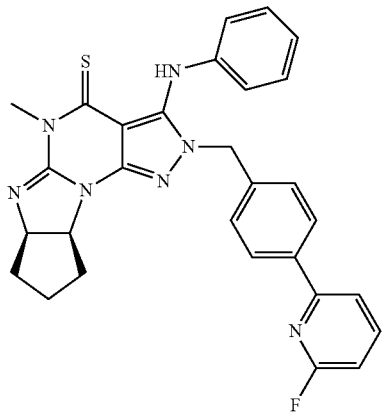 [SMILES: CN1C(=S)c2c(nn(Cc3ccc(-c4cccc(F)n4)cc3)c2Nc2ccccc2)N2C1=N[C@@H]1CCC[C@@H]12]

The synthetic procedure of this compound is analogous to EXAMPLE 2 wherein (6aR,9aS)-5,6a,7,8,9,9a-hexahydro-5-methyl-3-(phenylamino)-2-(4-(6-fluoropyridin-2-yl)-benzyl)-cyclopent[4,5]imidazo[1,2-c]pyrazolo[4,3-e]pyrimidin-4(2H-1)-one is used instead of (6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e] pyrimidin-4(2H)-one. MS (ESI) m/z 524.2 [M+H]⁺.

Example 8

(6aR,9aS)-5,6a,7,8,9,9a-hexahydro-5-methyl-3-(phenylamino)-2-(4-(6-mercapto-pyridin-2-yl)-benzyl)-cyclopent[4,5]imidazo[1,2-a]pyrazolo[4,3-e]pyrimidin-4(2H)-thione

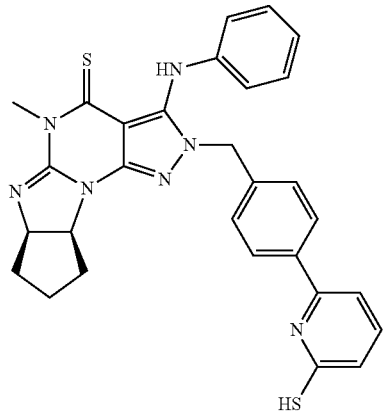 [SMILES: CN1C(=S)c2c(nn(Cc3ccc(-c4cccc(S)n4)cc3)c2Nc2ccccc2)N2C1=N[C@@H]1CCC[C@@H]12]

The synthetic procedure of this compound is the same as EXAMPLE 7. (6aR,9aS)-5,6a,7,8,9,9a-hexahydro-5-methyl-3-(phenylamino)-2-(4-(6-mercapto-pyridin-2-yl)-benzyl)-cyclopent[4,5]imidazo[1,2-a]pyrazolo[4,3-e]pyrimidin-4(2H)-thione is obtained as the major product of the reaction. MS (ESI) m/z 538.2 [M+H]⁺.

Example 9

(6aR,9aS)-2,5,6a,7,8,9,9a-heptahydro-4-imino-3-(phenylamino)-2-((4-Pyridin-2-yl)-benzyl)-cyclopent[4,5]imidazo[1,2-a]pyrazolo[4,3-e]pyrimidine

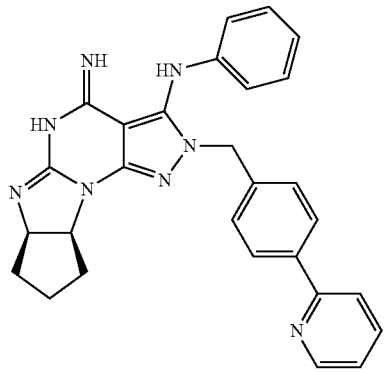 [SMILES: N=C1NC2=N[C@@H]3CCC[C@@H]3N2c2nn(Cc3ccc(-c4ccccn4)cc3)c(Nc3ccccc3)c21]

The synthetic procedure of this compound is analogous to EXAMPLE 4 wherein (6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-thione is used instead of (6aR,9aS)-5,6a,7,8,9,9a-hexahydro-5-methyl-3-(phenylamino)-2-((4-trifluoromethyl-benzyl)- cyclopent[4,5]imidazo[1,2-a]pyrazolo[4,3-e]pyrimidin-4(2H)-thione. MS (ESI) m/z 475.2 [M+H]+.

Example 10

(6aR,9aS)-5,6a,7,8,9,9a-hexahydro-5-methyl-3-(4-fluoro-phenylamino)-2-((4-Pyridin-4-yl)-benzyl)-cyclopent[4,5]imidazo[1,2-a]pyrazolo[4,3-e]pyrimidin-4(2H)-thione

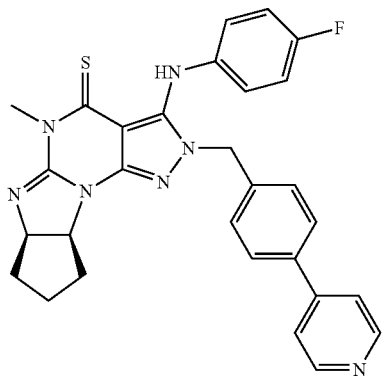 [SMILES: CN1C(=S)c2c(nn(Cc3ccc(-c4ccncc4)cc3)c2Nc2ccc(F)cc2)N2C1=N[C@@H]1CCC[C@@H]12]

The synthetic procedure of this compound is analogous to EXAMPLE 2 wherein (6aR,9aS)-5,6a,7,8,9,9a-hexahydro-5-methyl-3-(4-fluoro-phenylamino)-2-((4-Pyridin-4-yl)-benzyl)-cyclopent[4,5]imidazo[1,2-a]pyrazolo[4,3-e]pyrimidin-4(2H)-one is used instead of (6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-one. MS (ESI) m/z 524.2 [M+H]+.

Example 11

(6aR,9aS)-2,5,6a,7,8,9,9a-heptahydro-5-methyl-3-(4-fluoro-phenylamino)-2-((4-Pyridin-4-yl)-benzyl)-cyclopent[4,5]imidazo[1,2-a]pyrazolo[4,3-e]pyrimidine

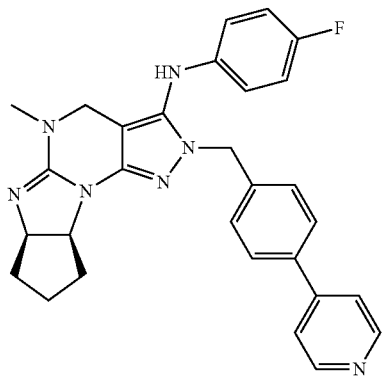 [SMILES: CN1Cc2c(nn(Cc3ccc(-c4ccncc4)cc3)c2Nc2ccc(F)cc2)N2C1=N[C@@H]1CCC[C@@H]12]

The synthetic procedure of this compound is analogous to EXAMPLE 1 wherein (6aR,9aS)-5,6a,7,8,9,9a-hexahydro-5-methyl-3-(4-fluoro-phenylamino)-2-((4-Pyridin-4-yl)-benzyl)-cyclopent[4,5]imidazo[1,2-a]pyrazolo[4,3-e]pyrimidin-4(2H)-one is used instead of (6aR,9aS)-5,6a,7,8,9,9a-hexahydro-5-methyl-3-(phenylamino)-2-((4-Pyridin-2-yl)-benzyl)-cyclopent[4,5]imidazo[1,2-a]pyrazolo[4,3-e]pyrimidin-4(2H)-one. MS (ESI) m/z 494.3 [M+H]+.

Example 12

Measurement of PDE1B Inhibition In Vitro Using IMAP Phosphodiesterase Assay Kit

Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization ($\Delta$mp). Inhibition of phosphodiesterase, therefore, is detected as a decrease in $\Delta$mp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization ($\Delta$mp).

A decrease in GMP concentration, measured as decreased Amp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows IC$_{50}$ values to be estimated using nonlinear regression software (XLFit; IDBS, Cambridge, Mass.).

The Compounds of the Invention may be selected and tested in an assay as described or similarly described herein for PDE1 inhibitory activity. The exemplified compounds of the invention generally have IC$_{50}$ values of less than 1 μM, some less than 250 nM, some less than 10 nM, some less than 1 nM, some with PDE1A activities e.g., the Compounds of Examples 1 and 2 generally have IC$_{50}$ values of less than 250 nM.

Example 13

PDE1 Inhibitor Effect on Sexual Response in Female Rats

The effect of PDE1 inhibitors on Lordosis Response in female rats may be measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg, 1.0 mg or 2.5 mg) or sesame oil vehicle (control). The rats are tested for lordosis response in the presence of male rats. Lordosis response is quantified by the lordosis quotient (LQ=number of lordosis/10 mounts×100).

What is claimed is:

1. An optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine, in free or salt form.

2. The compound according to claim 1, wherein said compound is a Compound of Formula I

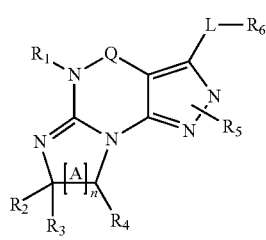

Formula I wherein
(i) Q is C(=S), C(=N(R$_{20}$)) or CH$_2$;
(ii) L is a single bond, —N(H)—, —CH$_2$—;
(iii) R$_1$ is H or C$_{1-4}$ alkyl;
(iv) R$_4$ is H or C$_{1-6}$ alkyl and R$_2$ and R$_3$ are, independently, H or C$_{1-6}$alkyl optionally substituted with halo or hydroxy, aryl, heteroaryl, (optionally hetero)arylalkoxy, or (optionally hetero)arylC$_{1-6}$alkyl;
or
R$_2$ is H and R$_3$ and R$_4$ together form a di-, tri- or tetramethylene bridge;
(v) R$_5$ is
a) -D-E-F, wherein:
D is C$_{1-4}$alkylene;
E is a single bond, C$_{2-4}$alkynylene, arylene or heteroarylene;
F is H, aryl, heteroaryl, halo, haloC$_{1-4}$alkyl, —C(O)—R$_{15}$, —N(R$_{16}$)(R$_{17}$), —S(O)$_2$R$_{21}$ or C$_{3-7}$cycloalkyl optionally containing at least one atom selected from a group consisting of N or O;

wherein D, E and F are independently and optionally substituted with one or more halo, C$_{1-4}$alkyl, haloC$_{1-4}$alkyl; or
b) a haloalkyl substituted heteroarylalkyl; or
c) attached to one of the nitrogens on the pyrazolo portion of Formula I and is a moiety of Formula A

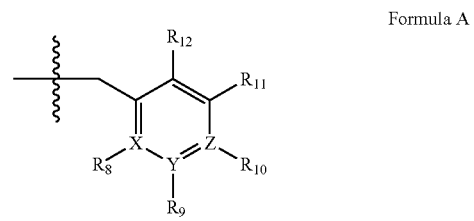

Formula A wherein X, Y and Z are, independently, N or C, and R$_8$, R$_9$, R$_{11}$ and R$_{12}$ are independently H or halogen, and R$_{10}$ is halogen, C$_{1-4}$alkyl, C$_{3-7}$cycloalkyl, C$_{1-4}$haloalkyl, aryl, heteroaryl, arylcarbonyl, alkylsulfonyl, heteroarylcarbonyl, or alkoxycarbonyl; provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl,
aryl,
heteroaryl,
arylC$_{1-4}$alkyl,
arylamino,
heteroarylamino,
N,N-diC$_{1-4}$alkylamino,
N,N-diarylamino,
N-aryl-N-(arylC$_{1-4}$alkyl)amino, or
—N(R$_{18}$)(R$_{19}$);
wherein the aryl or heteroaryl is optionally substituted with one or more halo, hydroxy or C$_{1-6}$alkoxy,
(vii) n=0 or 1;
(viii) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy or (optionally hetero)arylC$_{1-4}$alkyl;
(ix) R$_{15}$ is C$_{1-4}$alkyl, haloC$_{1-4}$alkyl, —OH or —OC$_{1-4}$alkyl;
(x) R$_{16}$ and R$_{17}$ are independently H or C$_{1-4}$alkyl;
(xi) R$_{18}$ and R$_{19}$ are independently H, C$_{1-4}$alky or aryl wherein said aryl is optionally substituted with one or more halo or hydroxy;
(xii) R$_{20}$ is H, C$_{1-4}$alkyl or C$_{3-7}$cycloalkyl,
(xiii) R$_{21}$ is C$_{1-6}$alkyl
in free or salt form.

3. The compound according to claim 1, selected from any of the following:

-continued

59
-continued
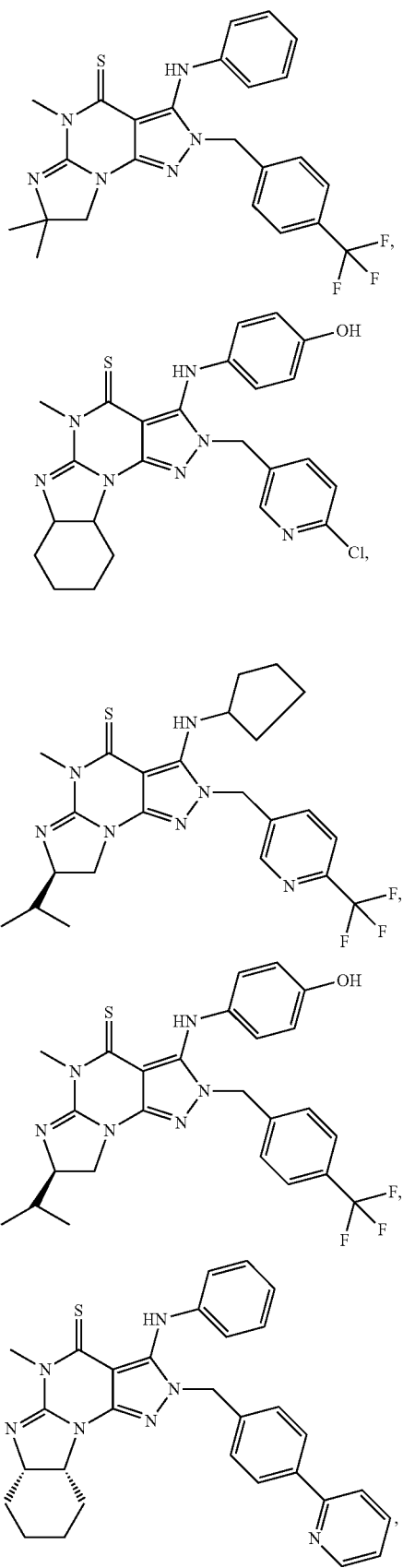
60
-continued
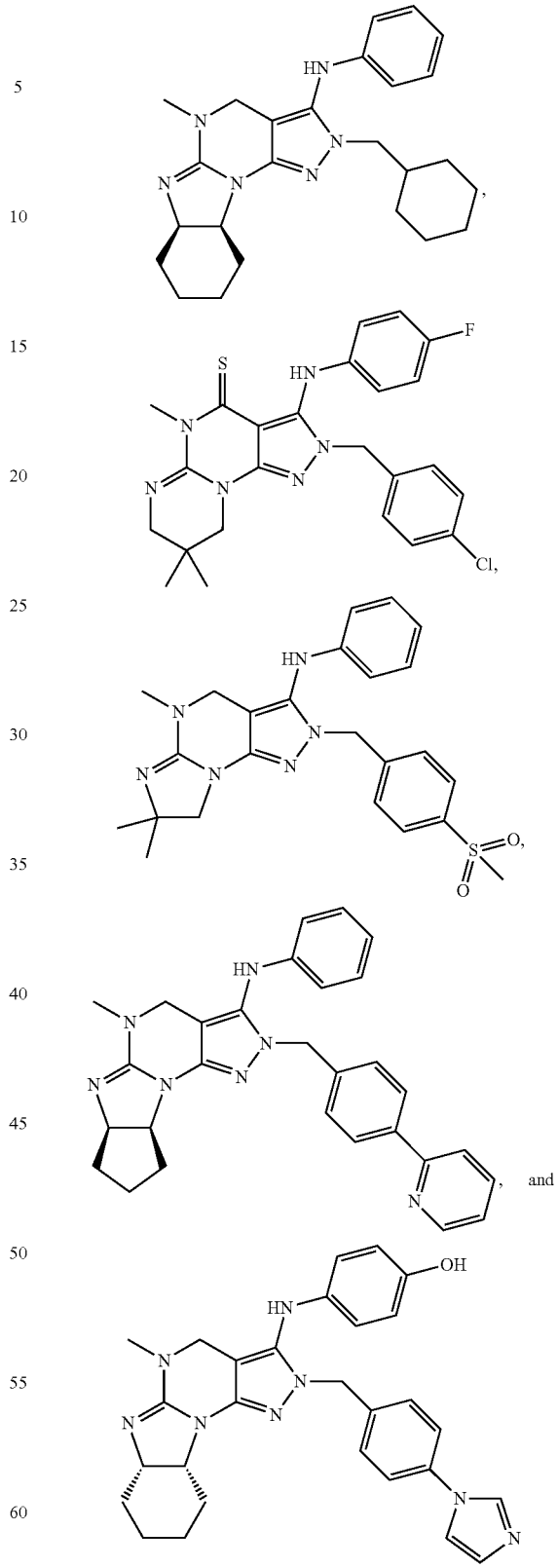
in free or salt form.
4. The compound according to claim 1, selected from any of the following:

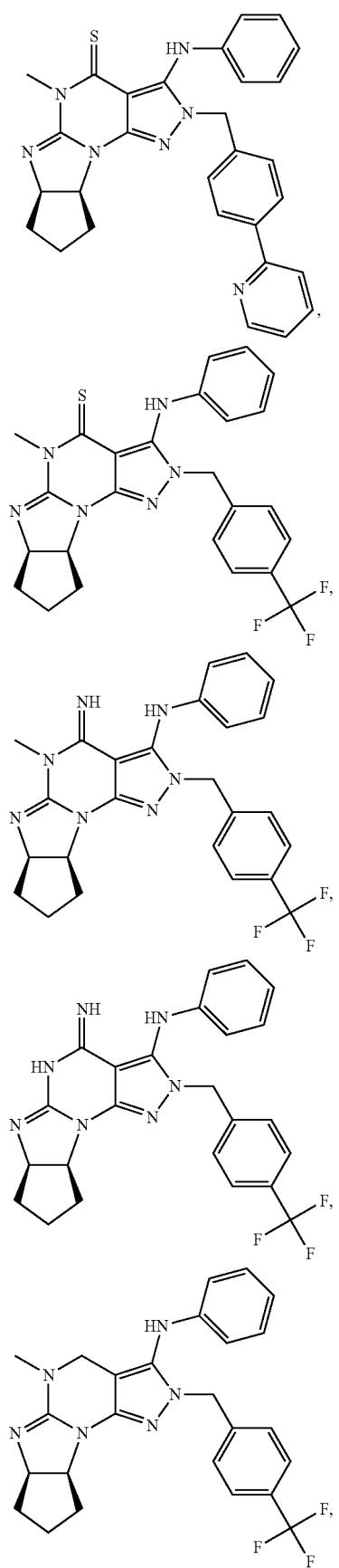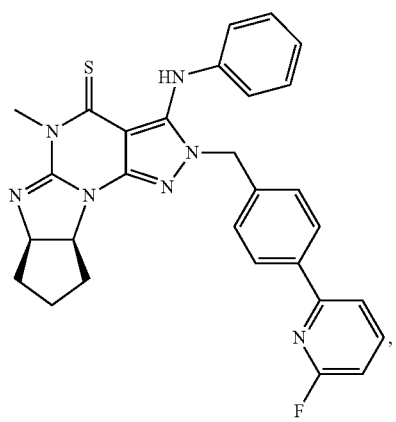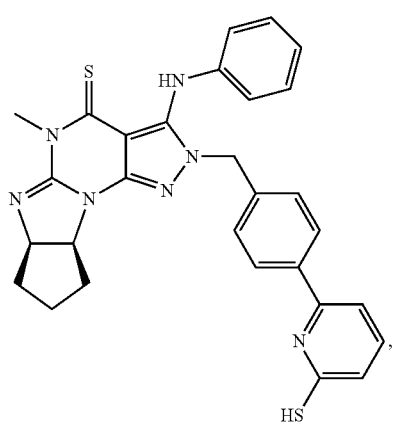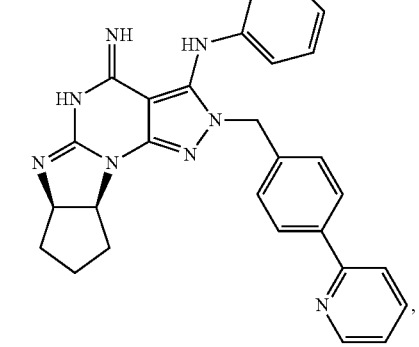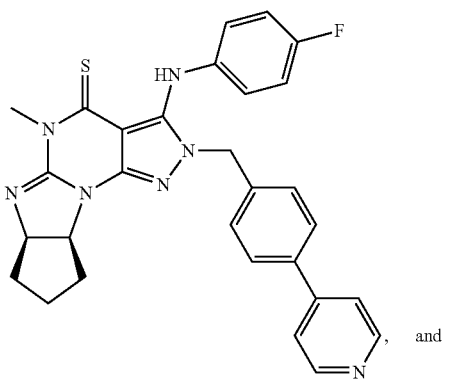

-continued

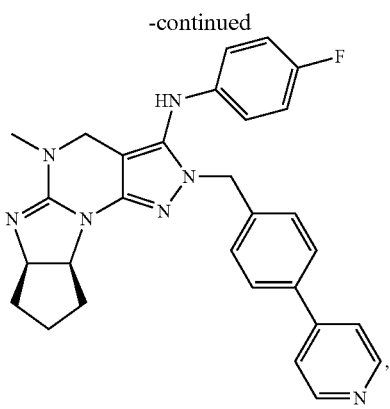

in free or salt form.

5. The compound according to claim 1, wherein said compound is a compound of formula II:

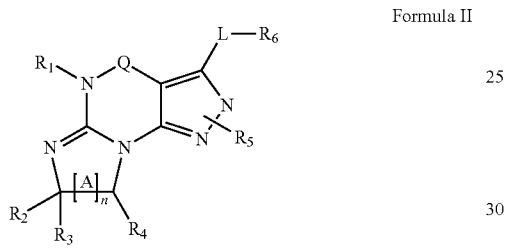

Formula II wherein
(i) Q is C(=S), C(=N(R$_{20}$)) or CH$_2$;
(ii) L is a single bond, —N(H)—, —CH$_2$—;
(iii) R$_1$ is H or C$_{1-4}$ alkyl;
(iv) R$_4$ is H or C$_{1-6}$ alkyl and R$_2$ and R$_3$ are, independently:
   H or C$_{1-6}$alkyl optionally substituted with halo or hydroxy,
   aryl,
   heteroaryl,
   (optionally hetero)arylalkoxy,
   (optionally hetero)arylC$_{1-6}$alkyl, or
   R$_2$ and R$_3$ together form a 3- to 6-membered ring;
   or
   R$_2$ is H and R$_3$ and R$_4$ together form a di-, tri- or tetramethylene bridge;
(v) R$_5$ is
   a) -D-E-F, wherein:
      D is C$_{1-4}$alkylene;
      E is a single bond, C$_{2-4}$alkynylene, arylene or heteroarylene;
      F is
         H,
         aryl,
         heteroaryl,
         halo,
         haloC$_{1-4}$alkyl,
         —C(O)—R$_{15}$,
         —N(R$_{16}$)(R$_{17}$),
         —S(O)$_2$R$_{21}$ or
         C$_{3-7}$cycloalkyl optionally containing at least one atom selected from a group consisting of N or O;
      wherein D, E and F are independently and optionally substituted with one or more:
         halo,
         C$_{1-4}$alkyl,
         haloC$_{1-4}$alkyl,
         C$_{1-4}$alkoxy or
         C$_{1-4}$alkyl;
         or
   b) a haloalkyl substituted heteroarylalkyl; or
   c) attached to one of the nitrogens on the pyrazolo portion of Formula II and is a moiety of Formula A

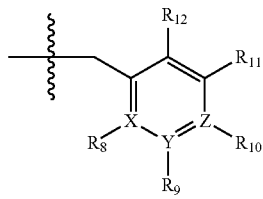

Formula A wherein X, Y and Z are, independently, N or C, and R$_8$, R$_9$, R$_{11}$ and R$_{12}$ are independently H or halogen, and R$_{10}$ is:
   halogen,
   C$_{1-4}$alkyl,
   C$_{3-7}$cycloalkyl,
   heteroC$_{3-7}$cycloalkyl,
   C$_{1-4}$haloalkyl,
   aryl,
   heteroaryl,
   arylcarbonyl,
   alkylsulfonyl,
   heteroarylcarbonyl, or
   alkoxycarbonyl;
   wherein the aryl, heteroaryl, cycloalkyl or heterocycloalkyl is independently and optionally substituted with one or more halo, C$_{1-4}$alkyl, C$_{1-4}$alkoxy, C$_{1-4}$haloalkyl, —SH;
   provided that when X, Y, or Z is nitrogen, R$_8$, R$_9$, or R$_{10}$, respectively, is not present;
(vi) R$_6$ is
   H,
   C$_{1-4}$alkyl,
   C$_{3-7}$cycloalkyl,
   aryl,
   heteroaryl,
   arylC$_{1-4}$alkyl,
   when L is a single bond, —N(H)—, or —CH$_2$—,
   wherein aryl or heteroaryl is optionally substituted with one or more halo, hydroxy, C$_{1-6}$alkyl, C$_{1-6}$alkoxy, C$_{3-8}$cycloalkyl;
   or R$_6$ is
   arylamino,
   heterarylamino,
   N,N-diC$_{1-4}$-alkylamino,
   N,N-diarylamino,
   N-aryl-N-(arylC$_{1-4}$alkyl)amino, or
   —N(R$_{18}$)(R$_{19}$);
   wherein the aryl or heteroaryl is optionally substituted with one or more halo, hydroxy, C$_{1-6}$alkyl, C$_{1-6}$alkoxy, C$_{3-8}$cycloalkyl;
(vii) n=0 or 1;
(viii) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{13}$ or R$_{14}$ can form a bridge with R$_2$ or R$_4$;

(ix) $R_{15}$ is $C_{1-4}$-alkyl, halo$C_{1-4}$alkyl, —OH or —O$C_{1-4}$alkyl;
(x) $R_{16}$ and $R_{17}$ are independently H or $C_{1-4}$alkyl;
(xi) $R_{18}$ and $R_{19}$ are independently
H,
$C_{1-4}$alky,
$C_{3-8}$cycloalkyl,
hetero$C_{3-8}$cycloalkyl,
aryl, or
heteroaryl,
wherein said aryl or heteroaryl is optionally substituted with one or more
halo,
hydroxy,
$C_{1-6}$alkyl,
halo$C_{1-6}$alkyl,
$C_{1-6}$alkoxy,
aryl,
heteroaryl, or
$C_{3-8}$cycloalkyl;
(xii) $R_{20}$ is H, $C_{1-4}$alkyl or $C_{3-7}$cycloalkyl,
(xiii) $R_{21}$ is $C_{1-6}$alkyl;
in free or salt form.

6. The compound according to claim 5, wherein
(i) Q is —C(═S)—;
(ii) L is a single bond;
(iii) $R_5$ is attached to one of the nitrogens on the pyrazolo portion of Formula II and is a moiety of Formula A

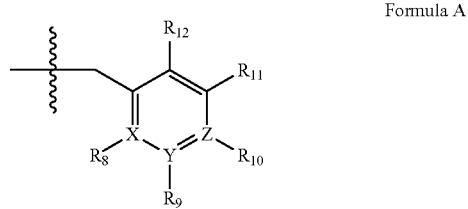

Formula A wherein X, Y and Z are, independently, N or C, and $R_8$, $R_9$, $R_{11}$ and $R_{12}$ are independently H or halogen, and $R_{10}$ is:
$C_{3-7}$cycloalkyl,
hetero$C_{3-7}$cycloalkyl,
aryl,
heteroaryl,
wherein the aryl, heteroaryl, cycloalkyl or heterocycloalkyl is independently and optionally substituted with one or more halo, $C_{1-4}$-alkyl, $C_{1-4}$alkoxy, $C_{1-4}$haloalkyl, —SH;
provided that when X, Y, or Z is nitrogen, $R_8$, $R_9$, or $R_{10}$, respectively, is not present;
(iv) $R_6$ is —N($R_{18}$)($R_{19}$) and $R_{18}$ and $R_{19}$ are independently
H,
$C_{1-4}$alkyl,
aryl, or
heteroaryl,
wherein said aryl or heteroaryl is optionally substituted with one or more
halo,
hydroxy,
$C_{1-6}$alkyl,
halo$C_{1-6}$alkyl,
$C_{1-6}$alkoxy,
aryl, or
heteroaryl, or $C_{3-8}$cycloalkyl;
in free or salt form.

7. The compound according to claim 2, wherein $R_6$ is phenyl optionally substituted with one or more halo, hydroxy or $C_{1-6}$alkoxy, in free or salt form.

8. The compound according to claim 7, wherein L is —N(H)—, in free or salt form.

9. The compound according to claim 8, wherein Q is C(═S), in free or salt form.

10. The compound according to claim 8, wherein Q is C(═N($R_{20}$)), in free or salt form.

11. The compound according to claim 8, wherein Q is $CH_2$, in free or salt form.

12. The compound according to claim 9, wherein $R_5$ is -D-E-F and D is methylene, E is phenylene and F is heteroaryl optionally substituted with one or more halo, $C_{1-4}$alkyl, halo$C_{1-4}$alkyl, in free or salt form.

13. The compound according to claim 12, wherein F is selected from 6-fluoropyrid-2-yl, 5-fluoropyrid-2-yl, 3-fluoropyrid-2-yl, 4-fluoropyrid-2-yl, in free or salt form.

14. The compound according to claim 9, wherein $R_5$ is -D-E-F and D is methylene, E is phenylene and F is halo$C_{1-4}$alkyl, in free or salt form.

15. The compound according to claim 9, wherein $R_5$ is -D-E-F and D is methylene, E is phenylene and F is pyridyl, in free or salt form.

16. The compound according to claim 1, wherein the compound is:

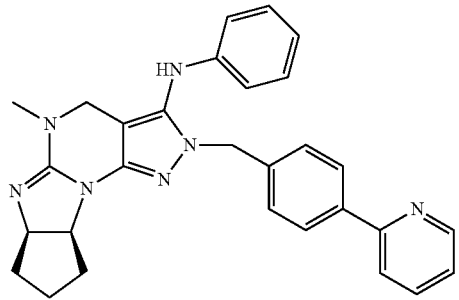 [SMILES: CN1Cc2c(nn(Cc3ccc(-c4ccccn4)cc3)c2Nc2ccccc2)N2C1=N[C@@H]1CCC[C@@H]12]

in free or salt form.

17. The compound according to claim 1, wherein the compound is:

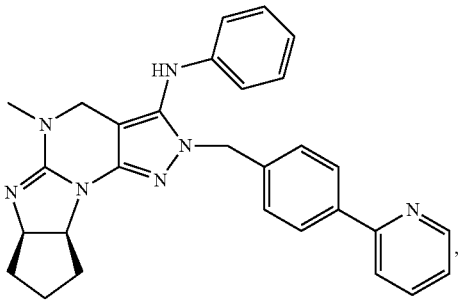

-continued

[chemical structures]

in free or salt form.

18. The compound according to claim 9, wherein $R_5$ is -D-E-F and:
D is methylene,
E is phenylene and
F is
aryl,
heteroaryl,
halo,
—C(O)—$R_{15}$ wherein $R_{15}$ is methyl; or
$C_{3-7}$cycloalkyl optionally containing at least one atom selected from a group consisting of N or O,
wherein D, E and F are independently and optionally substituted with one or more halo, $C_{1-4}$alkyl, halo$C_{1-4}$alkyl;
in free or salt form.

19. The compound according to claim 9, wherein $R_5$ is attached to one of the nitrogens on the pyrazolo portion of Formula II and is a moiety of Formula A Formula A

[structure with $R_{12}$, $R_{11}$, $R_8$, $R_9$, $R_{10}$, X, Y, Z]

wherein X, Y and Z are, independently, N or C, and $R_8$, $R_9$, $R_{11}$ and $R_{12}$ are independently H or halogen and $R_{10}$ is pyridyl or thiadiazolyl, in free or salt form.

20. The compound according to claim 9, wherein $R_5$ is attached to one of the nitrogens on the pyrazolo portion of Formula II and is a moiety of Formula A

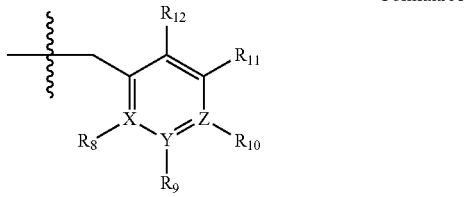

Formula A wherein X, Y and Z are, independently, N or C, and $R_8$, $R_9$, $R_{11}$ and $R_{12}$ are independently H or halogen and $R_{10}$ is haloalkyl, in free or salt form.

21. A pharmaceutical composition comprising a compound according to any of claim 5, in admixture with a pharmaceutically acceptable diluent or carrier.

22. A method of treating any of the following conditions: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling; comprising administering an effective amount of a compound according to claim 5, in free or pharmaceutically acceptable salt form, to a patient in need of such treatment.

23. The method of claim 22, wherein the condition is Parkinson's disease.

24. The method of claim 22, wherein the condition is cognitive impairment.

25. The method of claim 22, wherein the condition is narcolepsy.

26. The method of claim 25 further comprising administering a compound or compounds selected from central nervous system stimulants, modafinil, antidepressants, and gamma hydroxybutyrate, to a patient in need thereof.

27. The method of claim 22, wherein said condition is female sexual dysfunction.

28. The method of claim 27, further comprising administering a compound or compounds selected from a group consisting of estradiol, estriol, estradiol esters, progesterone and progestins to a patient in need thereof.

29. A method for the treatment of treatment for glaucoma or elevated intraocular pressure comprising topical administration of a therapeutically effective amount of a compound according to claim 5, in free or pharmaceutically acceptable salt form, in an opthalmically compatible carrier to the eye of a patient in need thereof.

30. A method for the treatment of psychosis, schizophrenia, schizoaffective disorder, schizophreniform disorder, psychotic disorder, delusional disorder, and mania, such as in acute manic episodes and bipolar disorder, comprising administering a therapeutically effective amount of a compound according to claim 5, in free or pharmaceutically acceptable salt form, to a patient in need thereof.

31. A method for the treatment of traumatic brain injury comprising administering to a patient in need thereof, a compound according to claim 5, in free or pharmaceutically acceptable salt form.

32. A method for lengthening or enhancing growth of the eyelashes by administering an effective amount of a prostaglandin analogue, concomitantly, simultaneously or sequentially with an effective amount of a compound according to claim 5, in free or salt form.

* * * * *